(12) United States Patent
Wang et al.

(10) Patent No.: US 11,826,194 B2
(45) Date of Patent: Nov. 28, 2023

(54) METHOD FOR MEASURING PARAMETERS IN ULTRASONIC IMAGE AND ULTRASONIC IMAGING SYSTEM

(71) Applicants: SHENZHEN MINDRAY BIO-MEDICAL ELECTRONICS CO., LTD., Guangdong (CN); SHENZHEN SECOND PEOPLE'S HOSPITAL, Guangdong (CN)

(72) Inventors: Huifang Wang, Shenzhen (CN); Yongquan Lai, Shenzhen (CN); Yaoxian Zou, Shenzhen (CN); Muqing Lin, Shenzhen (CN); Zhijie Chen, Shenzhen (CN)

(73) Assignees: Shenzhen Mindray Bio-Medical Electronics Co., Ltd., Shenzhen (CN); Shenzhen Second People's Hospital, Shenzhen (CN)

(*) Notice: Subject to any disclaimer, the term of this patent is extended or adjusted under 35 U.S.C. 154(b) by 301 days.

(21) Appl. No.: 16/478,094

(22) PCT Filed: Jan. 16, 2017

(86) PCT No.: PCT/CN2017/071277
§ 371 (c)(1),
(2) Date: Jan. 17, 2020

(87) PCT Pub. No.: WO2018/129737
PCT Pub. Date: Jul. 19, 2018

(65) Prior Publication Data
US 2020/0383658 A1    Dec. 10, 2020

(51) Int. Cl.
*A61B 8/08*     (2006.01)
*A61B 8/00*     (2006.01)
*A61B 5/00*     (2006.01)

(52) U.S. Cl.
CPC .......... *A61B 8/085* (2013.01); *A61B 5/7267* (2013.01); *A61B 8/463* (2013.01); *A61B 8/467* (2013.01)

(58) Field of Classification Search
CPC ....... A61B 8/085; A61B 5/7267; A61B 8/463; A61B 8/467; A61B 8/485; A61B 8/486;
(Continued)

(56) References Cited

U.S. PATENT DOCUMENTS 8,699,766 B2    4/2014  Cong et al.
10,426,438 B2   10/2019 Roh et al.
(Continued)

FOREIGN PATENT DOCUMENTS

CA    2839854 A1    7/2015
CN    102113897 A    7/2011
(Continued)

OTHER PUBLICATIONS

First Search dated Jun. 28, 2021, issued in related Chinese Application No. 201780079237.5 (3 pages).
(Continued)

*Primary Examiner* — Baisakhi Roy
*Assistant Examiner* — Kaitlyn E Sebastian
(74) *Attorney, Agent, or Firm* — Sheppard Mullin Richter & Hampton LLP

(57) ABSTRACT

A method for measuring parameters in an ultrasonic image, comprising: acquiring an ultrasonic image, the image comprising a target tissue; an ultrasound probe obtaining an ultrasonic image by means of receiving an ultrasound signal from the target tissue; displaying the ultrasonic image; obtaining a measurement instruction on the basis of the ultrasonic image; calculating a related measurement item of the target tissue according to the measurement instruction and obtaining a calculation result; and outputting the calcu-
(Continued)

lation result. Further provided is a system for measuring parameters in an ultrasonic image. The method and system solve the problem wherein ultrasonic image measurement operations are inconvenient.

19 Claims, 13 Drawing Sheets

(58) Field of Classification Search
CPC ........... A61B 8/488; A61B 8/06; A61B 8/483; A61B 8/5223
See application file for complete search history.

(56) References Cited

U.S. PATENT DOCUMENTS

| | | | |
|---|---|---|---|
| 2004/0210136 A1* | 10/2004 | Varghese | A61B 8/08 600/443 |
| 2005/0215899 A1* | 9/2005 | Trahey | A61B 5/0048 600/439 |
| 2009/0316967 A1 | 12/2009 | Dardenne et al. | |
| 2011/0158490 A1* | 6/2011 | Cong | A61B 8/543 382/128 |
| 2011/0172531 A1* | 7/2011 | Kanayama | A61B 8/483 600/443 |
| 2014/0185895 A1* | 7/2014 | Swamy | A61B 8/0866 382/131 |
| 2014/0276872 A1* | 9/2014 | Song | A61F 2/4609 606/91 |
| 2016/0000401 A1* | 1/2016 | Mienkina | G16H 50/30 600/443 |
| 2016/0275678 A1* | 9/2016 | Onal | G06K 9/4642 |
| 2017/0007161 A1 | 1/2017 | Zou et al. | |
| 2017/0011252 A1* | 1/2017 | Yang | A61B 8/54 |
| 2017/0124700 A1* | 5/2017 | Sarojam | A61B 8/46 |
| 2018/0000447 A1* | 1/2018 | Stindel | A61B 8/4245 |
| 2021/0128020 A1 | 5/2021 | Zou et al. | |
| 2022/0087636 A1 | 3/2022 | Wang et al. | |

FOREIGN PATENT DOCUMENTS

| | | |
|---|---|---|
| CN | 102274051 A | 12/2011 |
| CN | 102727184 A | 10/2012 |
| CN | 103565470 A | 2/2014 |
| CN | 103750865 A | 4/2014 |
| CN | 104394771 A | 3/2015 |
| CN | 104921753 A | 9/2015 |
| CN | 105555198 A | 5/2016 |
| WO | 2015/139267 A1 | 9/2015 |

OTHER PUBLICATIONS

First Office Action dated Jul. 5, 2021, issued in related Chinese Application No. 201780079237.5, with English machine translation (29 pages).
Liqian Sun et al., "Transperineal pelvic ultrasound in evaluation of pelvic floor function in post-hysterectomy women", Chin. J. Med. Ultrasonic (electronic edition), vol. 12, No. 3, pp. 228-232, Mar. 2015, with English abstract.
PCT International Search Report and the Written Opinion dated Oct. 27, 2017, issued in related International Application No. PCT/CN2017/071277 (7 pages).
PCT International Preliminary Report on Patentability dated Jul. 25, 2019, issued in related International Application No. PCT/CN2017/071277, with English machine translation (10 pages).
Non-Final Office Action dated Dec. 12, 2022, issued in related U.S. Appl. No. 17/544,203 (17 pages).
Non-Final Office Action dated Dec. 21, 2022, issued in related U.S. Appl. No. 17/544,276 (19 pages).
Non-Final Office Action dated Dec. 30, 2022, issued in related U.S. Appl. No. 17/544,330 (22 pages).
Final Office Action dated Apr. 6, 2023, issued in related U.S. Appl. No. 17/544,203 (32 pages).
Notice of Allowance dated Apr. 21, 2023, issued in related U.S. Appl. No. 17/544,276 (10 pages).
Notice of Allowance dated Apr. 21, 2023, issued in related U.S. Appl. No. 17/544,330 (11 pages).

* cited by examiner

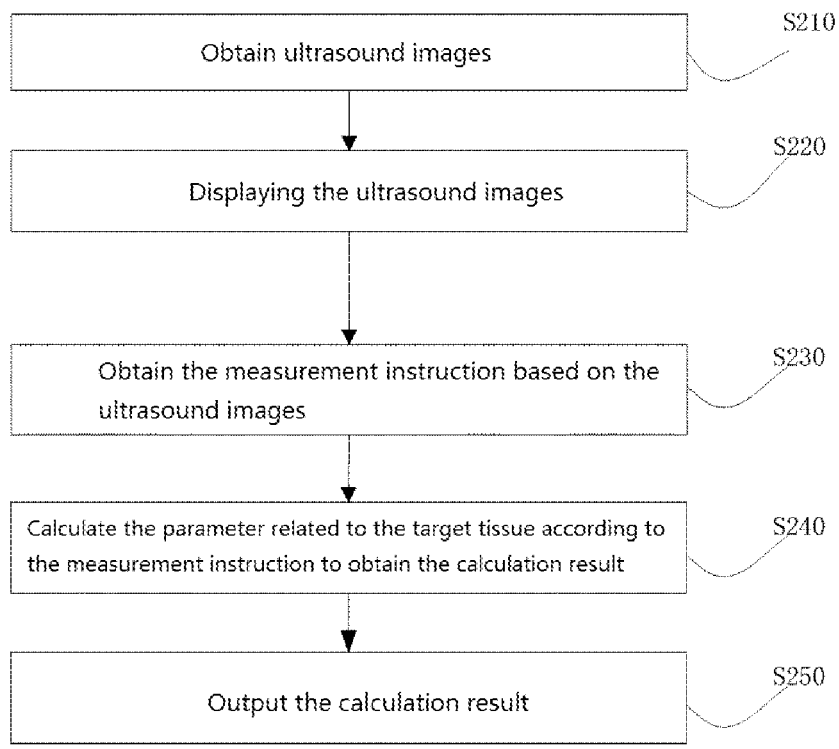
FIG. 2
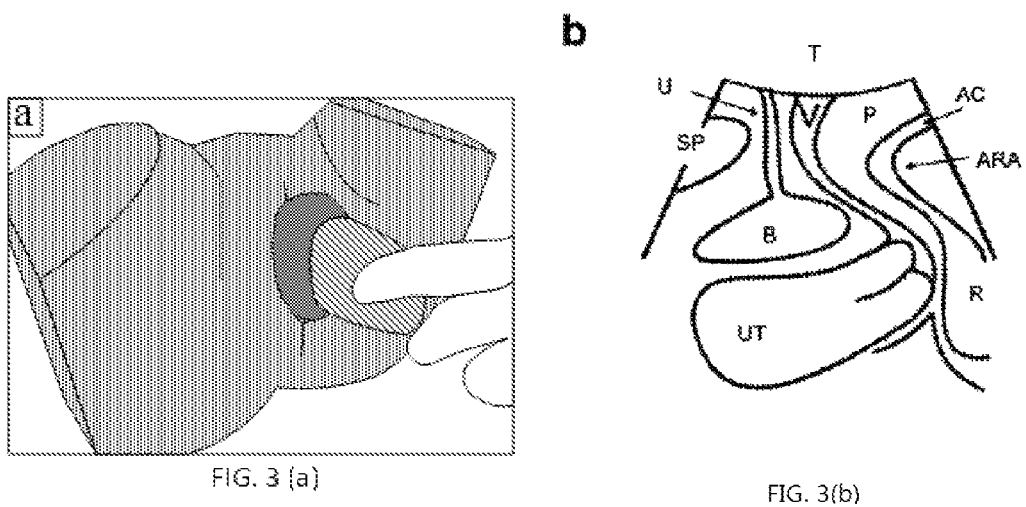
FIG. 3 (a)
FIG. 3(b)

METHOD FOR MEASURING PARAMETERS IN ULTRASONIC IMAGE AND ULTRASONIC IMAGING SYSTEM

CROSS-REFERENCE TO RELATED PATENT APPLICATION

This application is a U.S. National Stage Application under 35 U.S.C. 371 of International Application No. PCT/CN2017/071277, filed on Jan. 16, 2017, the contents of which is incorporated herein by reference in its entirety in the present disclosure.

TECHNICAL FIELD

The present disclosure relates to ultrasonic imaging devices, and particularly to methods and systems for performing parameter measurement in an ultrasonic image.

BACKGROUND

An ultrasound imaging device is used to image the inside of a target tissue, and, based on the characteristics of some medical parameters, to perform measurements on the image obtained by the ultrasound imaging, thereby enabling the doctor to obtain the actual anatomical structure parameters of the target tissue of the patient being examined. For example, Pelvic Floor Ultrasound (PFU) refers to a subject that uses the medical ultrasound device to scan and image women's pelvic floor, and plays an important role in the diagnosis of gynecological urology and other pelvic floor dysfunctions. Compared with other imaging methods such as MRI and cystourethrography, PFU has the advantages of low cost, non-invasiveness, convenient and quick examination, etc., and has gradually become the main method for diagnosing female pelvic floor dysfunction.

There are many examination items for pelvic floor ultrasound, and the doctors usually need to perform the measurement by drawing points in the image for each parameter, which leads to extra work. In addition, obtaining the amount of change and relative relationship between some parameters require additional calculation, which also brings a lot of inconvenience to the operator.

Of course, when there are multiple parameter items for the same target tissue, all of them are usually measured by drawing points, which brings the problem of inconvenience in operation.

SUMMARY

Based on this, it is desired to provide a method and system for measuring parameters in an ultrasound image in view of the inconvenience of operation in the prior art.

In one embodiment, a method for measuring a parameter in an ultrasound image is provided, which may include:
  obtaining an ultrasound image, where the ultrasound image may contain a target tissue area and be acquired by receiving, with an ultrasound probe, ultrasound signals from the target tissue;
  displaying the ultrasound image;
  obtaining a measurement instruction based on the ultrasound image;
  calculating a parameter related to the target tissue according to the measurement instruction to obtain a calculation result; and
  outputting the calculation result.

In one embodiment, an ultrasound imaging system is provided, which may include:
  a probe;
  a transmitting circuit and a receiving circuit which may be configured to excite the probe to transmit an ultrasonic beam to a target tissue and receive ultrasonic echoes of the ultrasonic beam to obtain an ultrasonic echo signal;
  an image processing unit which may be configured to obtain an ultrasound image according to the ultrasound echo signal;
  a display which may be configured to display the ultrasound image; wherein,
  the image processing unit may further be configured to obtain a measurement instruction based on the ultrasound image, calculate a parameter related to the target tissue according to the measurement instruction to obtain a calculation result and output the calculation result.

BRIEF DESCRIPTION OF THE DRAWINGS

FIG. 2 is a schematic flowchart of a method in one embodiment;

FIG. 3 (a) schematically shows the placement of the probe in translabial/transperineal ultrasound imaging;

FIG. 3 (b) schematically shows the median sagittal section image obtained thereby;

DETAILED DESCRIPTION

Figure 1:
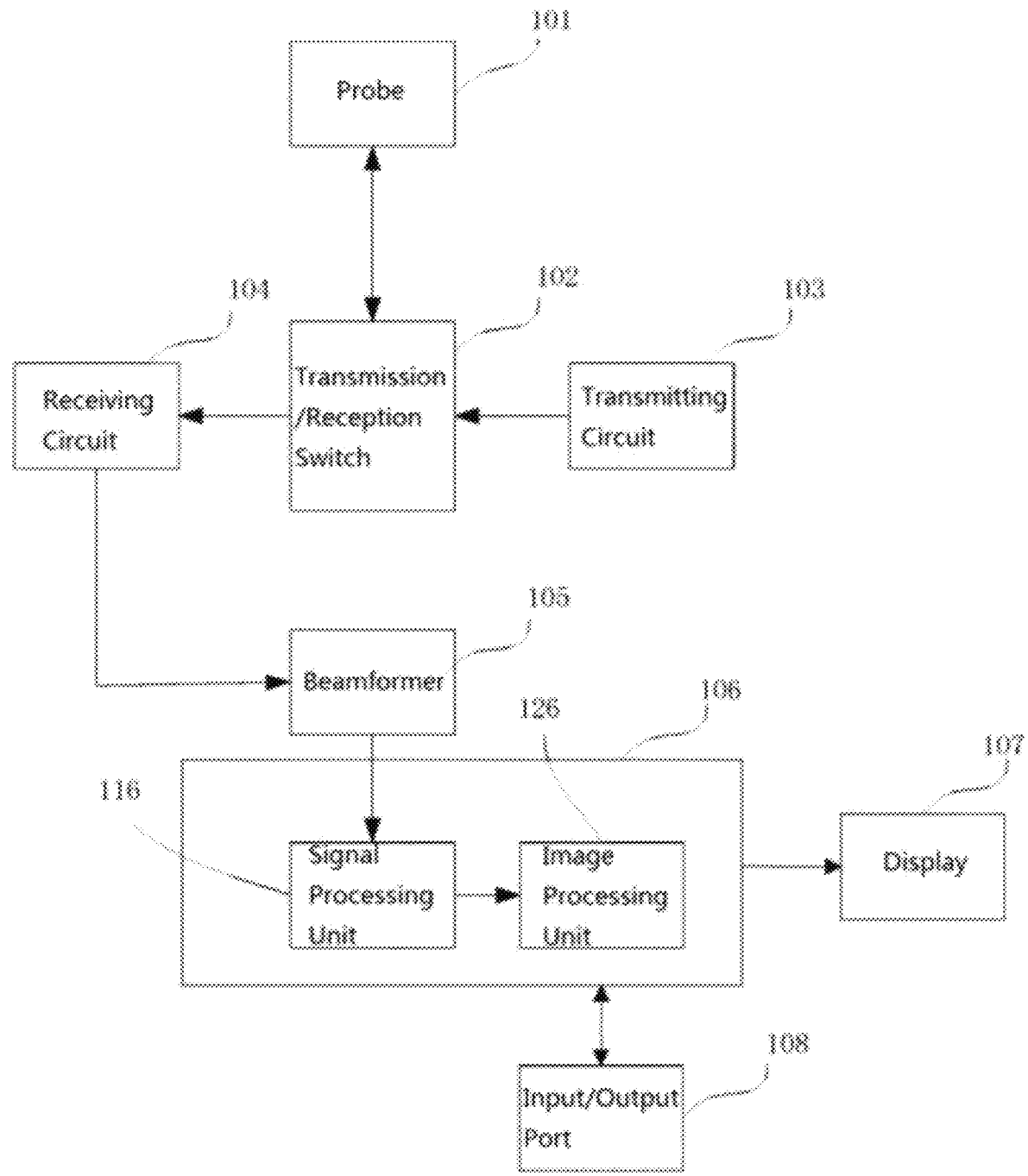
FIG. 1 is a schematic diagram of a configuration of an ultrasound imaging system in one embodiment.

The ultrasound imaging system shown in FIG. 1 may include a probe 101, a transmitting circuit 103, a transmission/reception switch 102, a receiving circuit 104, a beamformer 105, a signal processing unit 116, and an image processing unit 126. During the ultrasound imaging process, the transmitting circuit 103 may send delay-focused transmission pulses with a certain amplitude and polarity to the probe 101 through the transmission/reception switch 102. The probe 101 may be excited by the transmission pulses to transmit ultrasonic waves to a target tissue (for example, organs, tissues, blood vessels, etc. in a human or animal body, not shown in the figure). After a certain delay, the probe 101 may receive the ultrasonic echoes which are reflected from the target area and carry the information of the target tissue, and convert the ultrasonic echoes into electrical signals. The receiving circuit 104 may receive the electrical signals converted by the probe 101 to obtain ultrasonic echo signals, and send the ultrasonic echo signals to the beamformer 105. The beamformer 105 may perform processing such as focus delay, weighting and channel summing on the ultrasonic echo signals, and then send the ultrasonic echo signals to the signal processing unit 116 where related signal processing may be performed thereon. The ultrasonic echo signals processed by the signal processing unit 116 may be sent to the image processing unit 126. The image processing unit 126 may perform different processing on the signals according to different imaging modes desired by the user to obtain ultrasound image data in different modes, and perform log compression, dynamic range adjustment and digital scan conversion, etc. on the data to obtain ultrasound images in different modes, such as B images, C images, D images, Doppler blood flow images, elastic images containing tissue elastic properties, etc., or other types of two-dimensional or three-dimensional ultrasound images. The elastic images may be obtained by transmitting ultrasonic waves to detect the characteristics of the shear waves inside the target tissue, or by transmitting ultrasonic waves to detect the deformation of the target tissue due to external forces, where the shear waves may be generated by external vibration or by excitation of ultrasonic waves transmitted into the target tissue.

In some embodiments of the present disclosure, the signal processing unit 116 and the image processing unit 126 may be integrated on a main board 106. Alternatively, one or two or more units of them may be integrated in one processor/controller chip.

The ultrasound imaging system may further include an input/output port 108, which may be disposed on the main board 106. The ultrasound imaging system may be connected to an input/output device through the input/output port 108, and may receive, through the input/output port 108, an instruction signal inputted through the input/output device. The instruction signal may include a control instruction for controlling the timing of the transmitting and receiving of the ultrasonic waves, an operation input instruction for editing or annotating, etc. the ultrasound images, an output instruction for reminding the user, or other types of instructions. Generally, the operation instruction obtained when a user edits, annotates, or performs other operation on the ultrasound image may be used for measurement of the target tissue. The input/output device may include one of, or a combination of more of, a keyboard, a mouse, a scroll wheel, a trackball, and a mobile input device (a mobile device with a touch display, a mobile phone, etc.), etc. The corresponding input/output port 108 may be a wireless communication device, a wired communication device, or a combination thereof. The input/output port 108 may also be implemented based on Universal Serial Bus (USB), a bus protocol such as Controller Area Network (CAN), and/or a wired network protocol, etc.

In addition, the ultrasound imaging system may further include a display 107 which may display the ultrasound image data from the image processing unit. The display 107 may be a touch screen display. The ultrasound imaging system may also be connected to another display through the input/output port to implement a dual-display system. In addition, the display in this embodiment may include one or multiple displays. The number of displays will not be limited in this embodiment. The displayed ultrasound image data (ultrasonic image) may be displayed on one display or on multiple displays simultaneously, and it is also possible that the parts of the ultrasound image are respectively synchronously displayed on multiple displays, which will not be limited in this embodiment.

As shown in FIG. 2, a flowchart of a method for measuring parameters in an ultrasound image is provided. The process of performing the parameter measurement method in this embodiment will be described in detail below with reference to FIG. 1.

In step S210, the image processing unit 126 in the ultrasound imaging system may acquire an ultrasound image which contains the target tissue. As shown in FIG. 1, the ultrasound image may be obtained by receiving the ultrasound signals from the target tissue with the ultrasound probe 101. The ultrasound signals in this embodiment will not be limited to the ultrasound echo signals mentioned above with reference to FIG. 1, but may also be ultrasound signals generated in the target tissue by, for example, a photoacoustic imaging method. In addition, the target tissue here may include, but not limited to, pelvic floor tissue. The pelvic floor tissue may include one or more anatomical tissue structures in a female pelvic cavity, such as uterus, labia, perineum, pelvis, symphysis pubis, etc. The ultrasound image containing the pelvic floor tissues may include, but not limited to, anterior pelvic ultrasound images and posterior pelvic ultrasound images, and may also include middle pelvic ultrasound images. The commonly used measurement items of pelvic floor ultrasound may be divided into three parts: anterior pelvic cavity measurement items, middle pelvic cavity measurement items and posterior pelvic cavity measurement items. The parameter measurement based on the anterior pelvic ultrasound image and the middle pelvic ultrasound image may be mainly performed on the median sagittal section image obtained using a translabial probe or a transperineal probe (as shown in FIG. 3(a) and FIG. 3(b), where FIG. 3(a) shows the placement of the translabial/transperineal ultrasound probe and FIG. 3(b) shows the median sagittal section image obtained thereby). The parameter measurement based on the posterior pelvic ultrasound image may be performed on the ultrasound image acquired using an intracavity probe (endoanal probe) or on a proper section image selected in the axis plane in a static 3D ultrasound image or a 4D ultrasound image acquired using a transperineal or transvaginal probe. Regarding the parameter measurement based on the posterior pelvic ultrasound image, the description of this embodiment will be based on the second case described above, that is, the example where the posterior pelvic ultrasound image is acquired using the transperineal or transvaginal probe will be described.

In step S220, the image processing unit 126 in the ultrasound imaging system may output the ultrasound image to the display where the ultrasound image will be displayed. See the description regarding the display 107 above. In this embodiment, the manner of displaying the ultrasound image will not be limited. For example, the ultrasound image may be displayed on multiple displays at the same time, or only on one display. Alternatively, the parts of the ultrasound image may be respectively displayed on multiple displays synchronously, thereby expanding the viewing angle of the ultrasound image. Furthermore, in one embodiment, the image processing unit 126 may transmit the ultrasound image to the display through a wireless or wired manner. The display may be a touch display on a mobile device. Furthermore, in one embodiment, the ultrasound image may be displayed on a first layer, where the first layer may be a software interface layer other than the layer for displaying the non-image data such as annotations, markers, text and cursors, etc. Correspondingly, the software interface layer for displaying the non-image data such as annotations, markers, text and cursors, etc. may be referred to as a second layer. The areas of the second layer which overlap the first layer may be set as being transparent so as to not block the ultrasound image and enhance the visibility and user-friendliness. Furthermore, the entire second layer may be set as being transparent.

In step S230, the image processing unit may obtain a measurement instruction based on the ultrasound image. In step S240, the image processing unit may calculate a parameter related to the target tissue according to the measurement instruction to obtain a calculation result.

In this embodiment, the measurement instruction may be automatically determined by the system based on the ultrasound image. Alternatively, the measurement instruction may be obtained based on a measurement operation of a user on the ultrasound image, or an input inputted by a user on the ultrasound image according to a system prompt.

The purpose of the measurement instruction is to calculate the parameter related to the target tissue. The medical meaning of some parameters will be described in detail below.

In academic and clinic, there are many parameters related to the anterior pelvic ultrasound image, most of which are related to the diagnosis of Pelvic Organ Prolapsed (POP) and Urinary Incontinence. In the present embodiment, the parameters that may be involved may include, but not limited to, the following.

Figure 5:
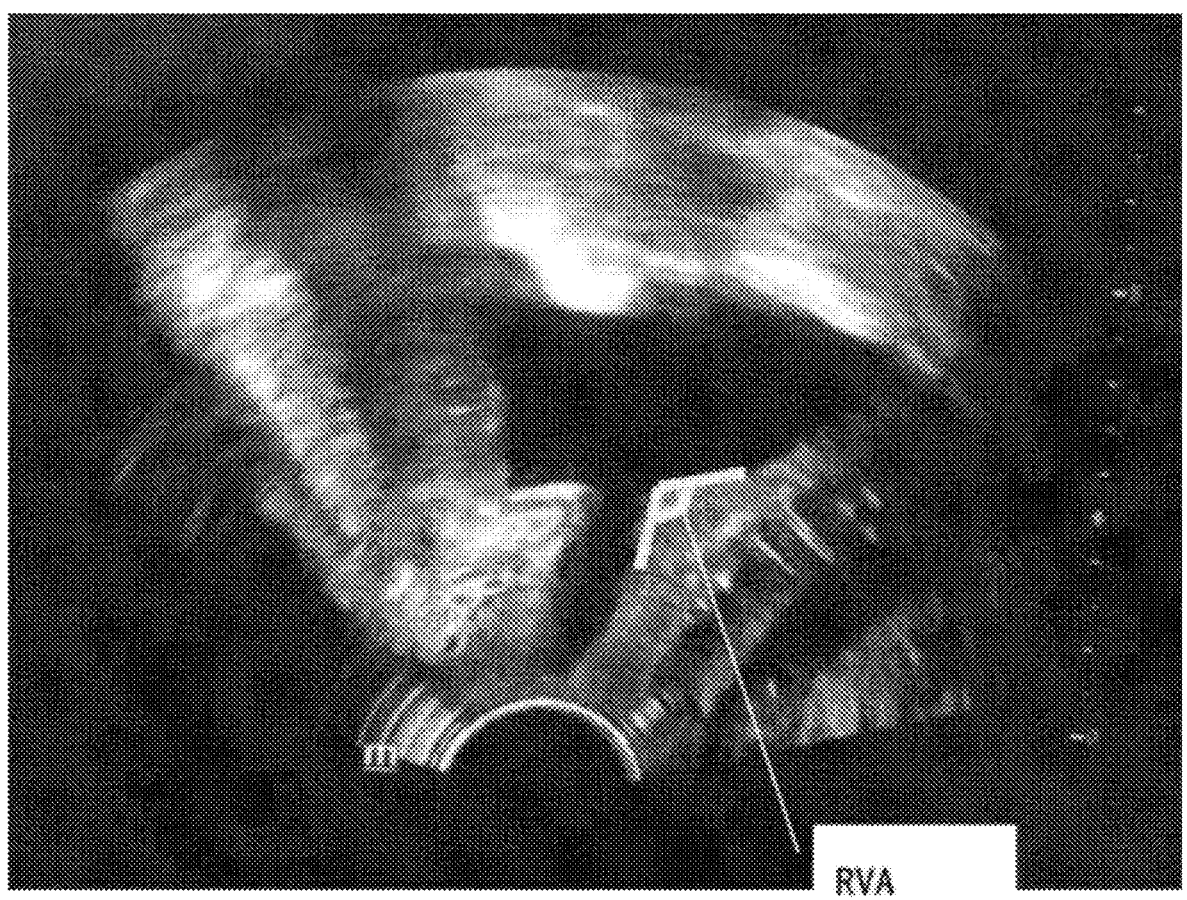
FIG. 5 schematically shows the posterior urethrovesical angle or retrovessel angle (RVA)
Figures 6A, 6B:
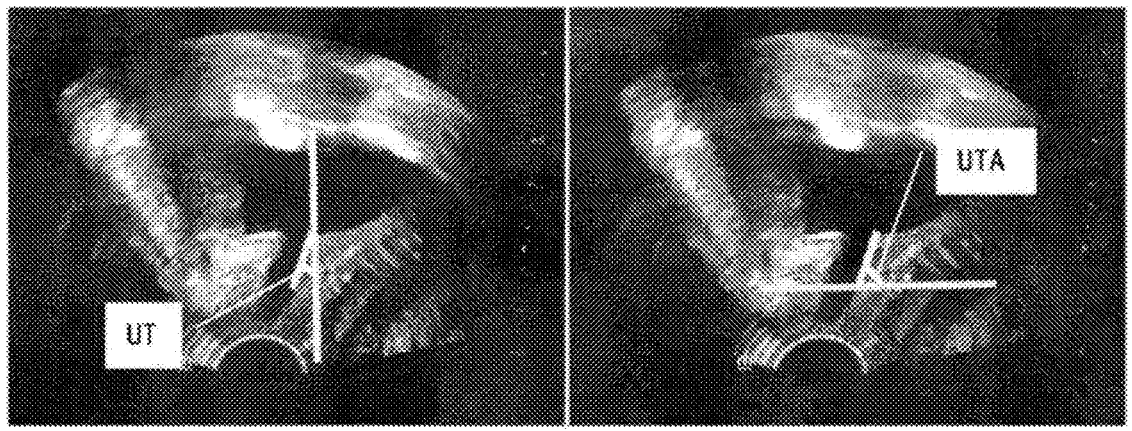
FIGS. 6 (a) and 6 (b) schematically shows two methods for calculating the urethral tilt angle (UTA)
Figures 7A, 7B:
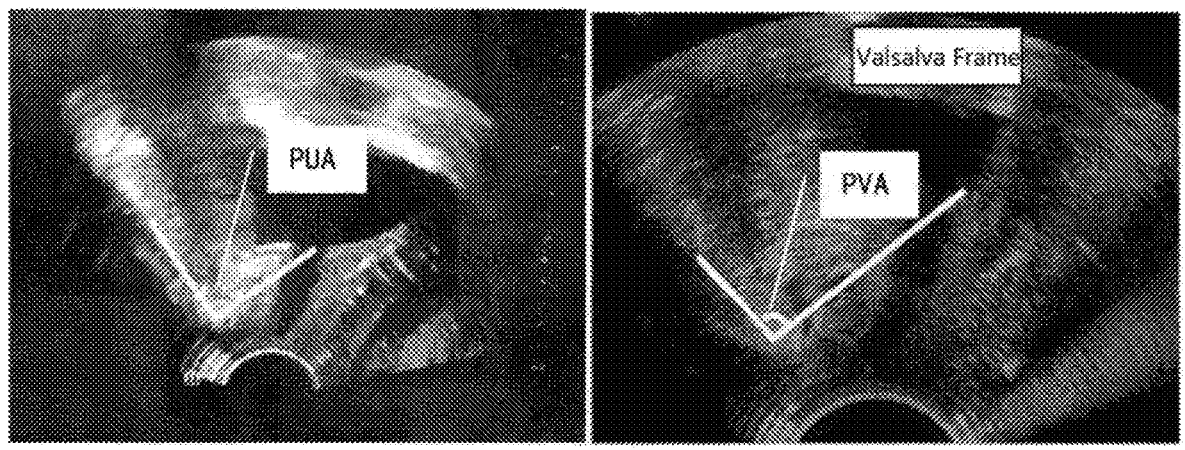
FIGS. 7 (a) and 7 (b) schematically shows the method for measuring the pubourethral angle and the pubovesical angle.

1) Posterior Urethro Vesical Angle or Retro Vesical Angle (RVA), as the angle shown in FIG. 5 with the white thick solid line in the image. The RVA is the angle between the proximal urethra and the rear end of the bladder triangle;

2) Urethral Tilt Angle (UTA) or Urethral Inclination (UI). FIG. 6(a) and FIG. 6(b) show two methods for calculating the UTA, where FIG. 6(b) shows the calculation method of Maglinte et al. The angles obtained by the two methods are mutually complementary. When the UTA is finally used to calculate the urethral rotation angle (URA), the two calculation methods are equivalent;

3) Pubo Urethral Angle (PUA). FIG. 7(a) shows the pubo urethral angle PUA, which is the angle between the central axis of the symphysis pubis and the line connecting the inferoposterior margin of the symphysis pubis and the bladder neck;

4) Bladder Neck-Symphyseal Distance (BSD) or Pubo Urethral Distance (PUD);

5) Pubo Vesical Angle (PVA). FIG. 7(b) shows the pubo vesical angle (PVA), which is the angle between the central axis of the symphysis pubis and the line connecting the inferoposterior margin of the symphysis pubis and the lowest point of the posterior wall of the bladder;

6) Pubo Vesical Distance (PVD) or Bladder Descent Max (BL Desc. Max);

7) Urethral Rotation Angle (URA);

8) Bladder Neck Descend or bladder neck mobility (BND); and

9) Bladder wall descend (BWD); etc.

A large part of these parameters depend on how to establish an appropriate reference coordinate system. For example, both BSD and PVD need a reference to the position of the symphysis pubis and its central axis, which depends on the establishment of a reference coordinate system with the central axis of the symphysis pubis being the X axis.

At the same time, there is relevance between these parameters. See FIG. 3(b) and the term explanations in the table below.

| English Name | Abbreviation | Definition |
|---|---|---|
| *Bladder neck | BN | Also be referred to as urethrovesical junction (UVJ), i.e. the junction of bladder and urethra |
| *Bladder neck descend | BND | The descending distance of the bladder neck in rest state and maximum valsalva state |
| *Urethrovesical junction | UVJ | I.e. BN |
| *Symphysis pubis, Pubissymphysis | SP, PS | From literatures and IUAG/ICS recommendations, the abbreviation SP is more commonly used |
| *Inferoposterior margin of the symphysis pubis | | Lower boarder of symphysis |
| *Internal urethral orifice | | I.e. BN or UVJ |
| *Proximal urethra | | The part of the urethra near the bladder. The end away from the bladder is referred to as distal urethra |
| Pelvic Floor Dysfunction | PFD | A collective name for various symptoms of the pelvic floor |
| Pelvic organ prolapsed, | POP | Generally referring to pelvic floor organs (such as the bladder, etc.) bulging from the vagina |
| LevatorAni muscle | LA | |

| English Name | Abbreviation | Definition |
| --- | --- | --- |
| Pelvic Floor Muscle Contraction | PFMC | When performing a 3D levator ani muscle imaging, the patient is usually required to perform an anal contraction action |
| Uterus | UT | |
| Bladder | B | |
| Urethra | U | |
| Vagina | V | |
| Perineum | P | |
| Ampullae Recti | R | |
| Anal Rectum angle | ARA | |
| Anal Canal | AC | |
| *PubourethralAngle | PUA | Also referred to as gamma angle |
| * Bladder Neck-Symphyseal Distance | BSD | The distance from UVJ (or BN) to the X axis of the coordinate system (according to another way, BSD is defined as the distance from the UVJ to the origin of the coordinate system) |
| *Posterior UrethroVesical Angle, | PUV, PUVA, RVA | Also referred to as retrovesical angle (RVA) or Beta angle |
| *PuboVesical angle | PVA | The angle between the central axis of the symphysis pubis and the line connecting the inferoposterior margin of the symphysis pubis and the lowest point of the posterior wall of the bladder |
| PuboVesicalDistance Or Bladder Descent Max | PVD BL Desc. Max | The distance from the lowest point of the posterior wall of the bladder to the X axis of the coordinate system |
| * Urethral Tilt Angle | UTA | The angle between the (proximal) urethra and the central axis of the human body, or the complementary angle thereof |
| *Urethral angle | UA | The urethral angle is defined as the angle between the distal urethra and the proximal urethra. Different from UTA and UR, UA represents the degree of curvature of the urethra itself |
| *Urethral rotation Angle | URA | The magnitude of the change of UTA A Cartesian coordinate system where the image center is the origin, the image width increasing direction is the positive direction of X axis and the image height increasing direction is the negative direction of Y axis |

Regarding the measurement of dynamic change, the user may perform the measurement on a second static frame after completing the measurement on a static frame. At this time, the system may display the measurement result of the second frame in real time, and at the same time calculate the change of certain measurement value relative to the first frame, such as:

1) the relative change of BSD, i.e. the descending distance of the bladder neck BND, 2) the relative change of PVD, i.e. the descending distance of the posterior wall of the bladder BWD, and 3) the relative change of UI, which corresponds to the urethral rotation angle UR.

When the measurement on the second frame is completed, if the user edits the input of the first frame, the dynamic change as shown above will also be updated and displayed in real time.

For example, URA, BND and BWD may be obtained through dynamic changes of UTA, BSD and PVD respectively; PUA and BSD, and PVA and PVD, depend on the same input information respectively; UTA/UR and PUA/BSD all depend on the determination of UVJ points. When the current ultrasound equipment is applied to the measurement of the pelvic floor, the existence of the above relevance is not taken into account, but they are usually summarized by the ultrasound doctor after measuring each item separately, which will definitely increase the burden on the doctor. Furthermore, because there is common information between the parameters, separate measurement of parameter will inevitably lead to measurement inconsistent and errors. For example, UTA, PUA, and BSD share the UVJ point. When measuring separately, the operator needs to select the UVJ point three times. The difference between these three selections will bring inconsistent measurement results.

Figure 4:
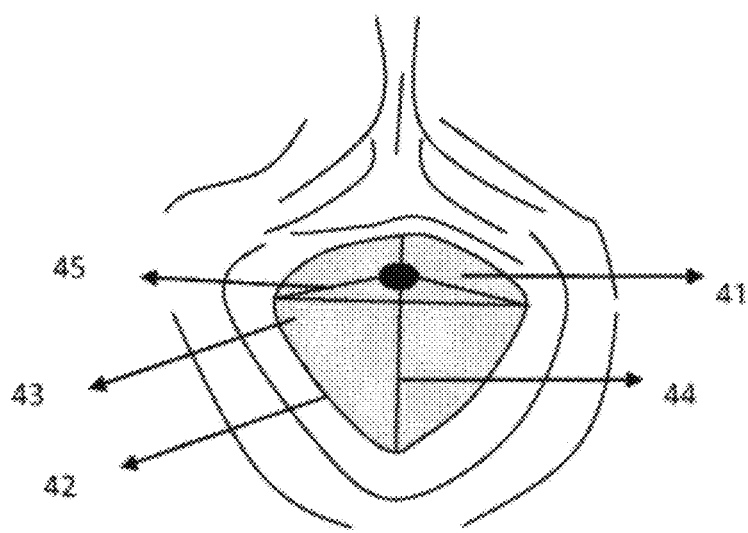
FIG. 4 schematically shows the measurement of the levator hiatus in the axial plane.

The parameters based on the posterior pelvic ultrasound image may be mainly used to evaluate the pelvic organ prolapsed and fecal incontinence. The common parameters are related to the levator ani muscle group, such as: (see FIG. 4)

a) Levator Hiatus area (LH Area), 41 in FIG. 4, b) Levator Hiatus Circumference (LHCirc), 42 in FIG. 4, c) the length of the Levator Hiatus anteroposterior diameter (LH AP, 44 in FIG. 4) and the Levator Hiatus Lateral Diameter (LH Lateral Diam, 43 in FIG. 4) of the levator hiatus, and d) Levator urethra gap (left and right) (LUG, 45 in FIG. 4), etc.

The parameters a to d mentioned above may be mainly related to the trace of the levator hiatus and the selection of the urethra. Ultrasound doctors usually use a trackball to perform curve tracing along the direction of the levator anus muscle, which is time-consuming and easy to misoperation. In addition, there are large differences between different operators and between different measurements of the same operator. These differences will undoubtedly affect the assessment of the degree of pelvic floor muscle tears, and may even cause missed diagnosis or misdiagnosis.

In order to reduce the burden on the doctors, improving the measurement efficiency and reducing the measurement errors are desired. In one embodiment, a new pelvic measurement method is proposed. In this method, the use of the relevance between parameters and the repetitiveness of input information are maximized. The positions of the measurement points may be inputted one by one in a programmable order, and the available measurement results may be updated and displayed in real time as the input information increases. This solution also well supports the automatic comprehensive summary of the results of two measurements, eliminating the inconvenience and possible errors caused by the operator's own calculations. In the following, the measurement based on the anterior pelvic ultrasound image will be described in detail.

The measurements based on the anterior pelvic ultrasound images may be performed on a two-dimensional median sagittal section image. The measurement process of the anterior pelvic cavity is complicated, which involves many parameters and usually needs to compare the measurement results of two frames. The first frame may be obtained by acquiring a median sagittal section image of the human body with a transperineal or transvaginal probe when the person being examined is in a relaxed state, which may also be referred to as a rest frame. The second frame may be obtained under the condition that the pelvic cavity of the person being examined is exerted downward to the maximum extent, which may also be referred to as valsalva frame and may be used to calculate the mobility of the pelvic floor organs such as the bladder and the urethra relative to the rest frame. The rest frame may be used as a reference image to calculate the amount of change of the valsalva frame relative to the rest frame.

Figure 8:
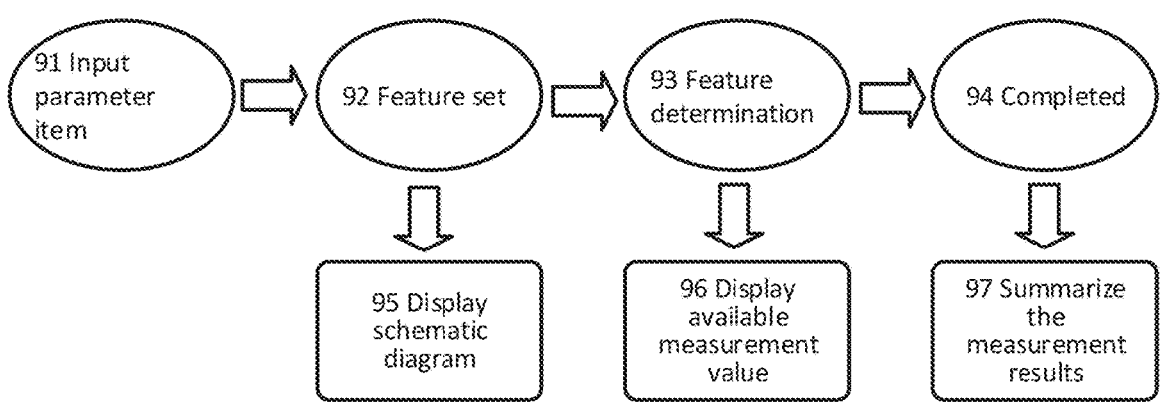
FIG. 8 is a schematic flowchart of a pelvic measurement method in one embodiment.

Different from the traditional scattered measurement solutions, the new pelvic measurement solutions proposed in this embodiment is more integrated. As shown in FIG. 8, to accomplish step S230 of FIG. 2 (the image processing unit obtains the measurement instruction based on the ultrasound image), the following process may be used.

In step 91, the input/output device (such as a keyboard, a mouse, a trackball, a touch screen or other human-computer interaction devices) may be used to receive at least one parameter item inputted by the user, and each parameter item may correspond to the position of at least one anatomical feature. Regarding the parameter items in this embodiment, reference may be made to the description above. One parameter item may correspond to a parameter of the target tissue, and one parameter may be calculated based on at least two anatomical features. The anatomical features herein may refer to the specific anatomical features associated with the parameter when the parameter of the target tissue is medically defined, such as the proximal urethra and the rear end of the bladder triangle associated with the posterior urethra vesical angle or retro vesical angle, the proximal urethra and the central axis of human body associated with the urethral tilt angle, the central axis of the symphysis pubis, the inferoposterior margin of the symphysis pubis and the bladder neck associated with the pubo urethral angle, the urethrovesical junction associated with the bladder neck descend, the central axis of the symphysis pubis, the inferoposterior margin of the symphysis pubis and the lowest point of the posterior wall of the bladder associated with the pubovesical angle, and the urethrovesical junction, etc. Reference may be made to the description above, and the anatomical features listed here are not in exhaustion. The anatomical feature may be an anatomical feature actually existing in the target tissue. Alternatively, the anatomical feature may be an anatomical reference line or reference position that is artificially defined in order to achieve the measurement of the target tissue. Image positions corresponding to the anatomical features may be identified on the ultrasound image. The image position may be a pixel, or a block or line area composed of multiple pixels. Alternatively, the image position may a neighborhood of a certain pixel.

In step 92, according to the inputted parameter item, at least one anatomical feature associated with the parameter item may be obtained to form a feature set to obtain the measurement instruction. In one embodiment, the feature set may be a group of anatomical features. The elements in the group may have three characteristics: 1. certainty (the elements in the group are certain); 2. mutual dissimilarity (the elements in the group are different from each other); 3. disorder (the elements in the group have no order). The feature set may be automatically obtained by the system based on the inputted parameter item.

In step 93, the position of each anatomical feature in the feature set may be determined according to the feature set, thereby obtaining the measurement instruction. In the step of determining the position of each anatomical feature in the feature set, the position of each anatomical feature in the feature set may be determined by the user clicking on the ultrasound image, thereby obtaining the measurement instruction; alternatively, the position of each anatomical feature in the feature set may be automatically identified by the system, thereby obtaining the measurement instruction. When the position of each anatomical feature is determined, a corresponding coordinate position in the measurement coordinate system may be accordingly determined. Therefore, the measurement instruction herein may include the information for determining the coordinate position of one or more anatomical feature in the feature set.

In step 94, the determination of the anatomical features in the feature set may be completed.

In step 97, the measurement results may be summarized.

In one embodiment, a step 95 may be further included, in which an anatomical schematic diagram may be displayed for prompting the feature sets. Alternatively, a text may be used to prompt the feature set. Both the anatomical schematic diagram and the text can be used to prompt the user to click on the ultrasound image to determine the position of each anatomical feature.

In one embodiment, a step 96 may be further included, in which an available measurement value may be displayed, i.e., the calculation result of the parameter obtained according to the measurement instruction may be displayed. The method for displaying the measurement value will be described in detail below.

Figure 9:
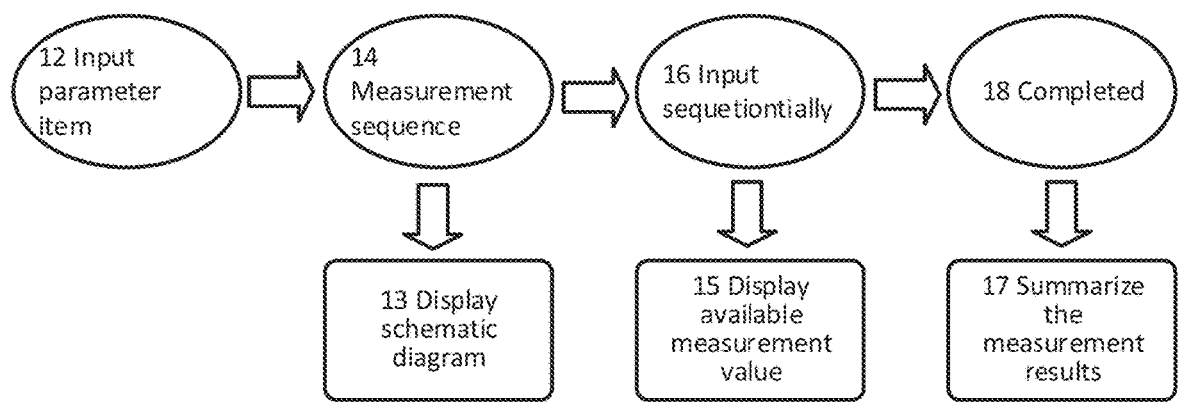
FIG. 9 is a schematic flowchart of a pelvic measurement method in another embodiment.

Referring to FIG. 9, in one embodiment, in step S230 (the image processing unit obtains the measurement instruction based on the ultrasound image), the following process may also be used.

In step 12, the input/output device (such as a keyboard, a mouse, a trackball, a touch screen or other human-computer interaction devices) may be used to receive at least one measurement item inputted by the user, and each measurement item may be related to at least one anatomical feature. This step may be the same as step 91 above.

In step 14, according to the inputted parameter item, at least one anatomical feature associated with the parameter item may be obtained to form a feature set, the determination order of the at least one anatomical feature when measuring the parameter may be determined according to the feature set, and the measurement sequence may be determined according to the feature set and the determination order. In one embodiment, the feature set may be a group of anatomical features. The measurement sequence may be automatically implemented by the system.

In step 16, the position of each anatomical feature in the feature set may be sequentially determined according to the feature set, thereby obtaining the measurement instruction. In the step of determining the position of each anatomical feature in the feature set, the position of each anatomical feature in the feature set may be determined by the user sequentially clicking on the ultrasound image according to the measurement sequence, thereby obtaining the measurement instruction; alternatively, the position of each anatomical feature in the measurement sequence may be automatically identified by the system, thereby obtaining the measurement instruction. When the position of each anatomical feature is determined, a corresponding coordinate position in the measurement coordinate system may be accordingly determined. Therefore, the measurement instruction herein may include the information for determining the coordinate position of one or more anatomical features in the feature set.

In step 18, the determination of the anatomical features in the measurement sequence may be completed.

In step 17, the measurement results may be summarized.

In one embodiment, a step 13 may be further included, in which an anatomical schematic diagram may be displayed for prompting the feature sets. Alternatively, a text may be used to prompt the feature set. Both the anatomical schematic diagram and the text can be used to prompt the user to click on the ultrasound image to determine the position of each anatomical feature.

In one embodiment, a step 15 may be further included, in which an available measurement value may be displayed, i.e., the calculation result of the parameter obtained according to the measurement instruction may be displayed. The method for displaying the measurement value will be described in detail below.

In the embodiments above, whether determining the position of each anatomical feature in the feature set according to the feature set to obtain the measurement instruction or sequentially determining the position of each anatomical feature in the feature set according to the measurement sequence, one of the following methods may be used to determine the position of each anatomical feature in the feature set to obtain the measurement instruction.

In the first method, the user's determination operation to one or more anatomical features in the feature set on the ultrasound image sequentially through the input/output device (which may include a keyboard, a mouse, a trackball, or a touch screen) may be received, and the measurement instruction may be obtained according to the determination operation inputted by the user. The order of the determination operation of the user may be an orderly operation performed according to the measurement sequence above. The orderly operation may be performed according to the determination order in the measurement sequence.

In the second method, the user's determination operation to one or more anatomical features in the feature set on the ultrasound image sequentially through the input/output device may be received, and the measurement instruction may be obtained according to the determination operations inputted by the user. The determination operations may be determination operations in any order. Here, determination operations in any order may also be understood as the determination operations that are completed without a determination order of the anatomical features given by the system or the manual.

The determination operation above may be used to determine the position of each anatomical feature in the ultrasound image.

In one embodiment, the feature set obtained in FIG. 8 or the position sequence obtained in FIG. 9 may be prompted. The feature set or measurement sequences may be prompted in the following ways.

Figure 10:
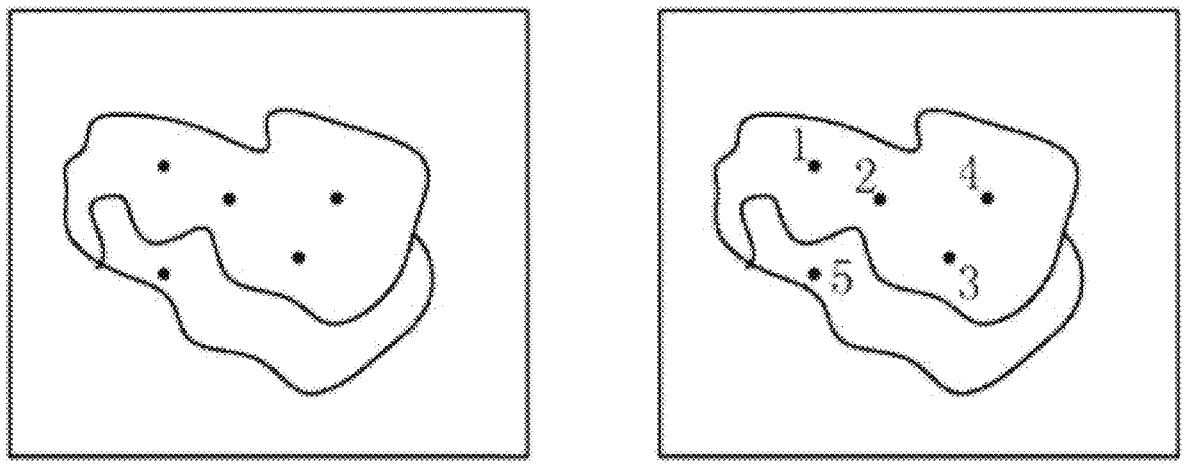
FIG. 10 is an anatomical schematic diagram of a target tissue.

First, based on the knowledge of tissue anatomy, an anatomical schematic diagram of the target tissue may be generated, as shown in FIG. 10.

Then, the anatomical schematic diagram may be displayed on the display. The anatomical schematic diagram may be displayed outside the area of the ultrasound image or on the ultrasound image. In one embodiment, the anatomical schematic diagram may be shown on the second layer mentioned above.

Thereafter, on the anatomical schematic diagram, the concentrated anatomical features may be marked (as shown in the left view in FIG. 10, in which the black dots indicate the anatomical features), or the measurement sequence above may be marked (as shown in the right view in FIG. 10). In the present embodiment, marking the measurement sequence may include marking the concentrated anatomical features in the feature set on the anatomical schematic diagram and marking the determination order of the determination operations of the anatomical features in the feature set (for example, the number in the right view in FIG. 10 may indicate the corresponding determination order of the anatomical features represented by the black dot). In addition to marking the determination order with the numbers in FIG. 10, it may also be possible that the anatomical feature currently to be determined is displayed by scrolling on the screen for prompting. In one embodiment, the method for the scrolling display may include sequentially displaying the anatomical feature currently to be determined in the feature set in any order or in the determination order.

Further, determining the position of each anatomical feature in the feature set to obtain the measurement instruction may further includes: determining a determination order corresponding to multiple anatomical features when measuring the parameter according to the measurement sequence, and prompting the multiple anatomical features to the user by scrolling text.

Because the pelvic floor examination may desire to compare the mobility of the organs in two acquired images, it is desired to find a fixed point in the two measurements to establish an appropriate reference coordinate system before the measurement. In one embodiment, the method for measuring the parameters in the ultrasound image may further include the following steps.

First, a reference coordinate system may be determined. The reference coordinate system may be at least one of a first Cartesian coordinate system with the inferoposterior margin of the symphysis pubis being the origin and the central axis of the symphysis pubis being the 45 degree angle of the second quadrant, a second Cartesian coordinate system with the inferoposterior margin of the symphysis pubis being the origin and the central axis of the symphysis pubis being the X axis and a third Cartesian coordinate system with the horizontal direction being the X axis and the vertical direction being the Y axis;

Then, in step S240, based on the determined reference coordinate system, the parameter may be calculated according to the measurement instruction.

Figure 11:
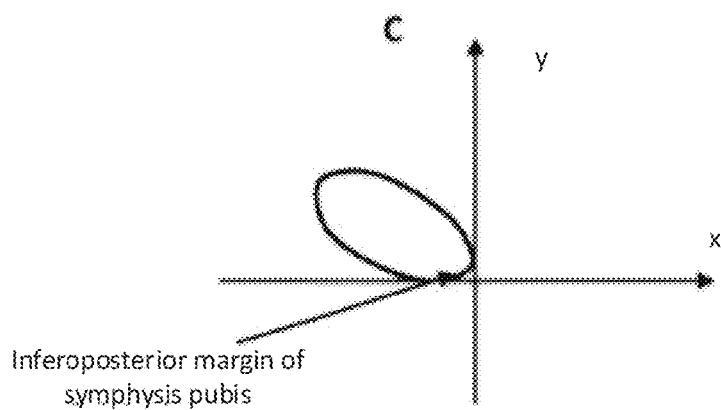
FIG. 11 is a schematic diagram of a reference coordinate system.

This embodiment may be compatible with at least three reference coordinate systems. As shown in FIG. 11, A is a Cartesian coordinate system with the inferoposterior margin of the symphysis pubis being the origin and the central axis of the symphysis pubis being the 45-degree angle of the second quadrant, B is a Cartesian coordinate system with the inferoposterior margin of the symphysis pubis being the origin and the central axis of the symphysis pubis being the x axis, and C is a Cartesian coordinate system with the horizontal direction being the x-axis and the vertical direction being the y-axis.

BSD/PVD may be calculated in different methods selected from the methods below for two different coordinate systems.

1) Measuring the distance from a point to the X axis of the coordinate system, or 2) Measuring the distance from a point to the Y axis of the coordinate system, or 3) Measuring the distance from a point to the origin of the coordinate system.

Figure 12:
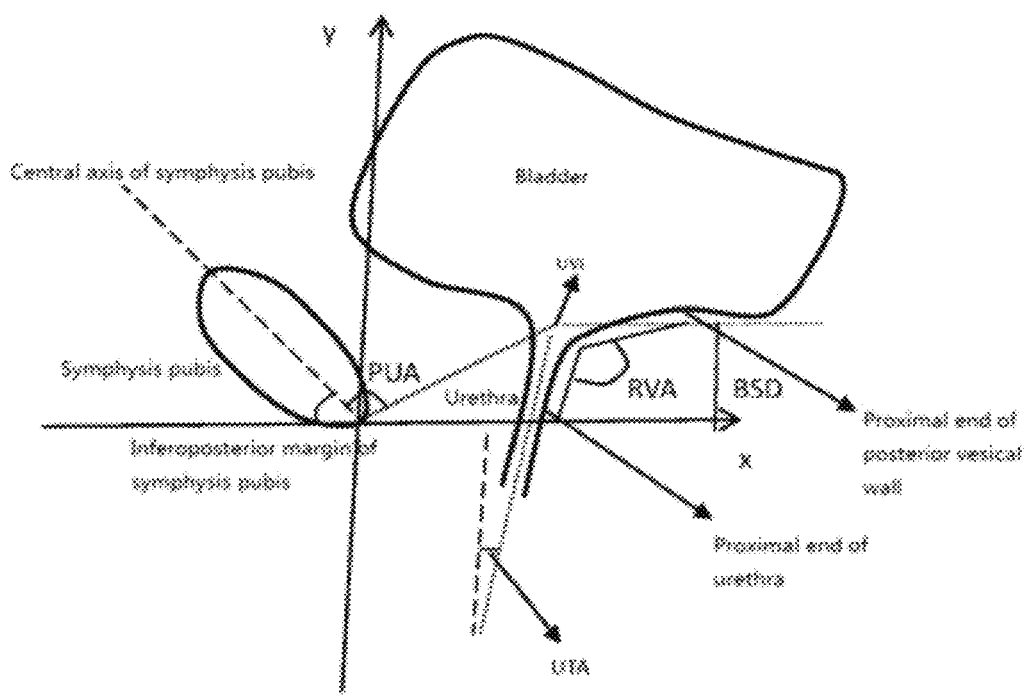
FIGS. 12 and 13 schematically show various parameter items of the pelvic floor.

Note: reference may be made to FIG. 12 which shows the first calculation method.

The user may select one of these three coordinate systems in the system preset options. For example, in one embodiment, the reference coordinate system may be determined in one of the following methods.

In the first method, the inferoposterior margin of the symphysis pubis and the central axis of the symphysis pubis inputted by the user on the ultrasound image may be received, and the first Cartesian coordinate system, the second Cartesian coordinate system or the third Cartesian coordinate system may be established according to the user input.

In the second method, the inferoposterior margin of the symphysis pubis and the central axis of the symphysis pubis may be automatically detected in the ultrasound image based on pattern recognition, and the first Cartesian coordinate system, the second Cartesian coordinate system or the third Cartesian coordinate system may be established thereby.

Alternatively, the following method may also be used. First, the options of at least three reference coordinate systems may be presented, and the reference coordinate systems may be selected from the first Cartesian coordinate system, the second Cartesian coordinate system and the third Cartesian coordinate system according to customer requirements; thereafter, a selection instruction for selecting the reference coordinate system inputted by the user may be received, and the reference coordinate system may be determined according to the selection instruction. The first Cartesian coordinate system, the second coordinate system, and the third Cartesian coordinate system may be obtained using the first method or second method described above.

When establishing a coordinate system based on the first method, whether being a 45-degree angle in the second quadrant or directly being the X axis of the coordinate system, the inferoposterior margin of the symphysis pubis and the central axis of the symphysis pubis are related to the establishment of the coordinate system. Therefore, the user may need to input the inferoposterior margin of the symphysis pubis and the central axis of the symphysis pubis. In this embodiment, two manual input solutions may be provided to receive the inferoposterior margin of the symphysis pubis and the central axis of the symphysis pubis inputted by the user on the ultrasound image.

Figure 16:
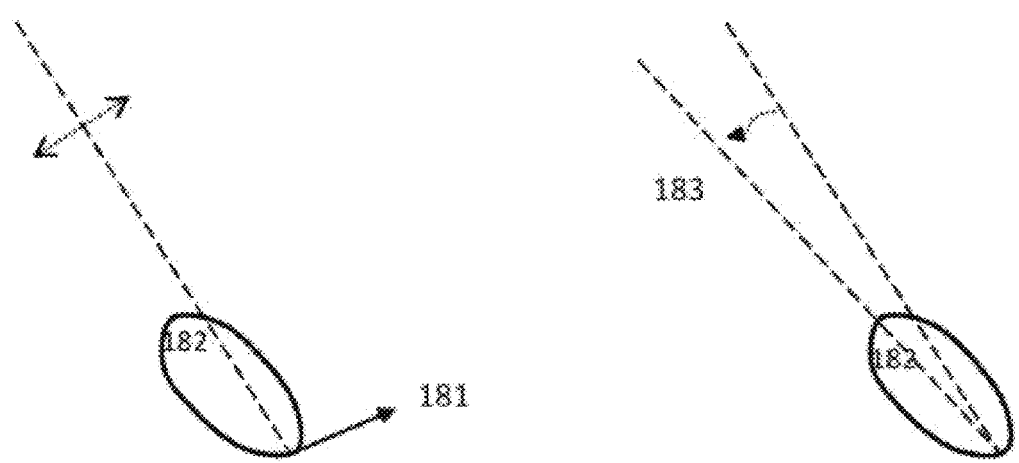

1) The user may first input the position information 181 of the inferoposterior margin of the symphysis pubis 182, as shown in the left view in FIG. 16. Then, as shown in the right view in FIG. 16, the user may operate an input device (such as a trackball) to determine the position 183 of the central axis. For example, in one embodiment, a click input may be received to determine the inferoposterior margin of the symphysis pubis. When the trackball or mouse or the touch contact with the display screen moves, the candidate center axis may moves therewith. When it is detected that the movement stopped, the candidate central axis may be displayed at the position where the movement stopped so as to determine the input of the central axis of the symphysis pubis. It should be noted that the position of the central axis may not have to be related to the absolute position of the cursor, and the system does not even need to display the mouse cursor. When the input device such as the mouse or the trackball moves, the candidate center axis may move accordingly until the operator notifies the system by operation such as clicking, etc. that the selection of the center axis position is completed.

2) The user may also directly input the positions of the two points to determine the position of the central axis of the symphysis pubis.

When establishing a coordinate system based on the second method, the two inputted points may also be automatically identified by the system. In this embodiment, a method for automatically determining a coordinate system is proposed, in which a mode recognition method may be used to automatically detect the inferoposterior margin of the symphysis pubis and the central axis of the symphysis pubis, thereby determining the position of the coordinate system. The following will describe how to detect these two anatomical positions.

In the automatic detection of the inferoposterior margin of the symphysis pubis, pattern recognition may be used to detect the inferoposterior margin of the symphysis pubis. In one embodiment, a positive image sample containing the inferoposterior margin of the symphysis pubis and a negative image sample not containing the inferoposterior margin of the symphysis pubis may be inputted to a detector for training; a recognition model may be obtained based on the training; and the inferoposterior margin of the symphysis pubis may be automatically detected in the ultrasound image using the recognition model. For example, first, the image patches of the inferoposterior margin of the symphysis pubis may be collected from a number of images that have been subjected a preprocessing such as smoothing or denoising, and be performed thereon certain normalization processing, which will be used as positive samples. The images that do not contain the inferoposterior margin of the symphysis pubis may be collected as background images. The image patch of any size in any position in these background images may be used as a negative sample. A specific detector may be trained using these positive samples and background images to detect the inferoposterior margin of the symphysis pubis. For example, the specific detector may include, but not limited to, the following detectors:

1) Cascade adaBoost detector using Haar features

2) Cascade adaBoost detector using Local Binary Patterns (LBP) features

3) Support Vector Machine (Latent SVM) detector

4) Detector based on neural network

Figure 27:
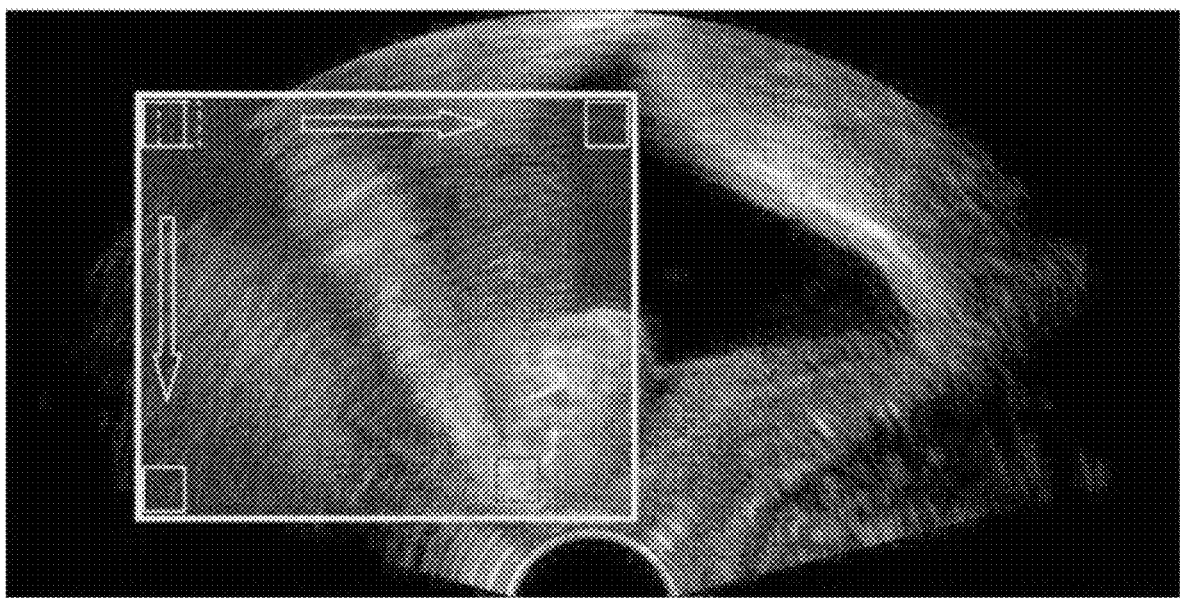
FIG. 27 shows an example of the detection range of the inferoposterior margin of the symphysis pubis.

In this embodiment, the type of the detector will not be limited, but be used as a part of an automatic measurement framework. Depending on the detector, the training method will be different. Regarding the detection, this method may use a search method based on a moving window (as shown in FIG. 27). In order to improve the detection efficiency, the area for detecting the symphysis pubis may be concentrated in certain possible area (for example, in the area of 0.1 w to 0.5 w, 0.1 h to 0.9 h). The window-type search may be performed in certain step length in pixels at different scales, and the most likely area may be selected therefrom. The search may be performed from left to right and top to bottom, and the most likely area may be selected therefrom. The symphysis pubis areas may be selected from a large number of images containing the symphysis pubis as the positive samples for training the detector. When the image is flipped or mirrored, the area for detection may be adjusted accordingly.

In the automatic detection of the central axis of the symphysis pubis, the starting point of the central axis of the symphysis pubis is determined as the inferoposterior margin of the symphysis pubis is determined. The rest is detecting the direction of the central axis of the symphysis pubis. In one embodiment, the process of automatically detecting the inferoposterior margin of the symphysis pubis and the central axis of the symphysis pubis in the ultrasound image based on pattern recognition may include the following steps.

Figure 25:
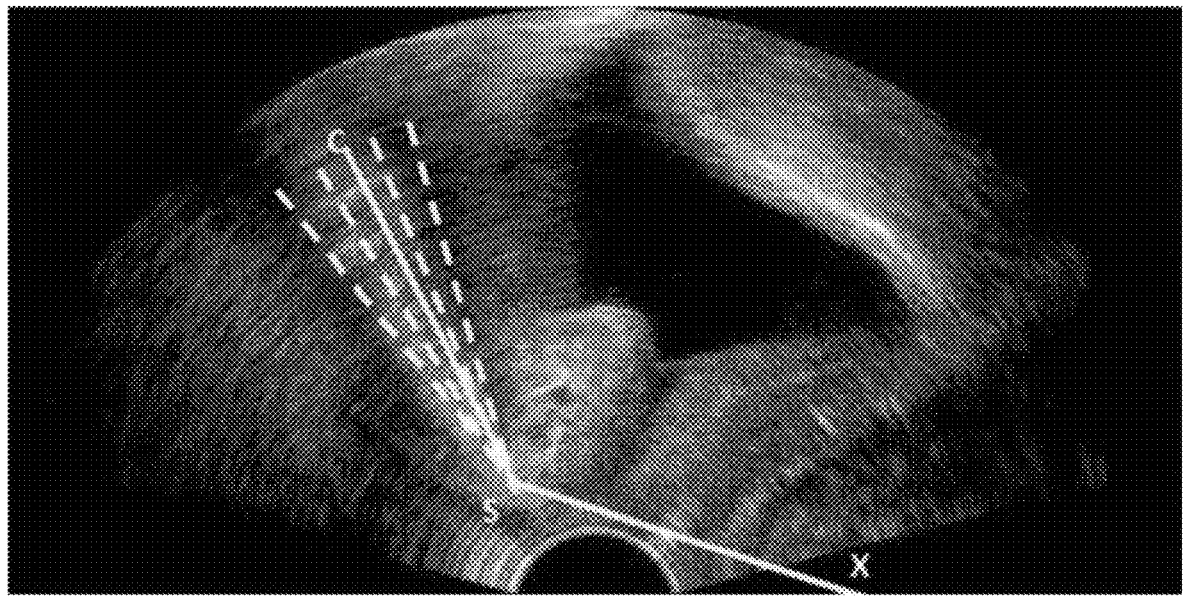
FIG. 25 schematically shows the positioning of the inferoposterior margin and the central axis of the symphysis pubis.

First, the starting point of the central axis of the symphysis pubis may be determined according to the inferoposterior margin of the symphysis pubis. A candidate ray representing the central axis of the symphysis pubis may be determined from the starting point. The candidate ray has initial deflection angle. Multiple candidate rays may be obtained in a predetermined range centered on the initial deflection angle and in predetermined intervals. For example, in a natural image Cartesian coordinate system, the search may be performed in a search range centered on a certain common angle of the symphysis pubis (such as 135 degree) in a certain interval of angle to obtain the most probable direction as the direction of the central axis of the symphysis pubis. As shown in FIG. 25. When the image is flipped or mirrored, the search rang may be adjusted accordingly. In FIG. 25, the ray sc may represent the initial deflection angle of the central axis of the symphysis pubis, and the dotted lines may represent multiple candidate rays. As shown in FIG. 25, the point S may be obtained by a detector (such as a cascaded adaboost classifier). The ray SC may be obtained by searching in a specific range (for example, in the natural image Cartesian coordinate system, the search may be performed in a range which is centered on 135-degree and formed by respectively deflecting 30 degree to the left and to the right, and in an interval of 1 degree, to obtain the most probable angle). After the ray SC is determined, the X axis may be obtained by rotating the SC ray clockwise 135 degrees around the S point (coordinate system C1) or directly using the ray SC as the X axis (coordinate system C).

Figure 26:
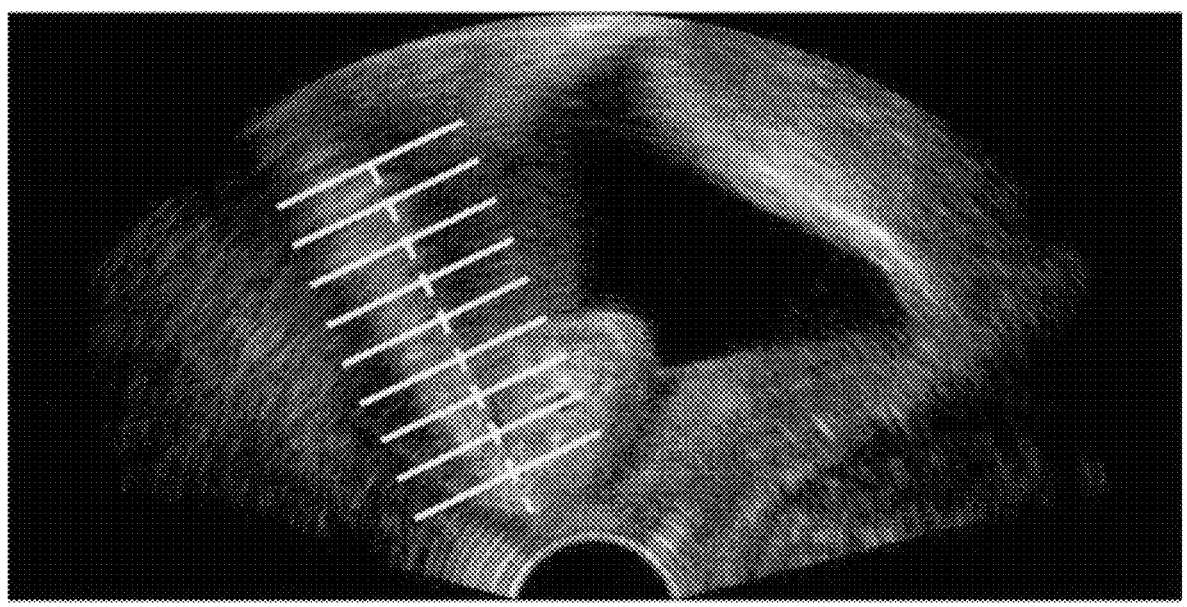
FIG. 26 schematically shows the method for extracting the characteristics of the central axis of symphysis pubis.

Second, the pixel characteristics of the multiple candidate rays may be extracted, and one of the multiple candidate rays may be determined as the central axis of the symphysis pubis based on the pixel characteristics. For example, for each candidate ray, characteristics related to said candidate ray may be extracted, such as selecting the pixel values on the normal lines at both sides of the candidate ray at certain intervals along the candidate ray as the characteristics, as shown in FIG. 26. The extracted characteristics may be inputted to a pre-trained detector and scored to obtain a group of scores (corresponding to a group of candidate rays). The candidate ray with the highest score may be determined as the central axis of the symphysis pubis.

There are a variety of detectors that can be used to detect the central axis of the symphysis pubis, such as a likelihood detector based on a Gaussian distribution or a detector based on (linear, polynomial, logistic, etc.) regression models, etc. The input of these detectors may be the characteristics equivalent to the characteristics inputted during the training phase, and the output may be continuous real number which represents the score to the input.

After the reference coordinate system is determined, the user may define the parameter items included in the measurement requirements (such as BSD, UTA, etc.) in advance, and the ultrasound imaging system may determine the anatomical feature to be inputted according to these measurement requirements, and automatically arrange the input order. The ultrasound imaging system may further display an anatomical schematic diagram on the screen to prompt the user how to perform a semi-automatic measurement operation according to the anatomical features automatically determined by the system. During the user determining the positions of the anatomical features according to the anatomical schematic diagram, the system may display the currently available measurement results in real time. It can be seen that, unlike the traditional separate measurement methods, the present embodiment proposes an integrated intelligent manual measurement method (see FIG. 8 and FIG. 9). Based on the process described in FIG. 9, the following illustrates how to perform the intelligent manual measurement.

In one embodiment, in step 12 in FIG. 9, the user may define the following parameter items through a preset menu:
(1) the angle PUA between the symphysis pubis and UVJ,
(2) the distance BSD from UVJ to X axis
(3) the urethral tilt angle UTA,
(4) the retrovesical angle RVA,
(5) the pubovesical angle PVA, and
(6) the distance PVD from the lowest point of the posterior wall of the bladder to the X axis.

In step 14, the ultrasound imaging system may automatically calculate the pelvic floor anatomical feature information needed to be inputted according to the logical relationship between these parameter items, i.e., determine the feature set of the anatomical features and generate a default measurement sequence, as follows. See FIG. 14.
(a) the lower boarder of SP,
(b) the central axis of SP,
(c) the urethrovesical junction (UVJ),
(d) the proximal end of urethra,
(e) the proximal end of posterior vesical wall, and
(f) the lowest point of posterior vesical wall.

Figure 13:
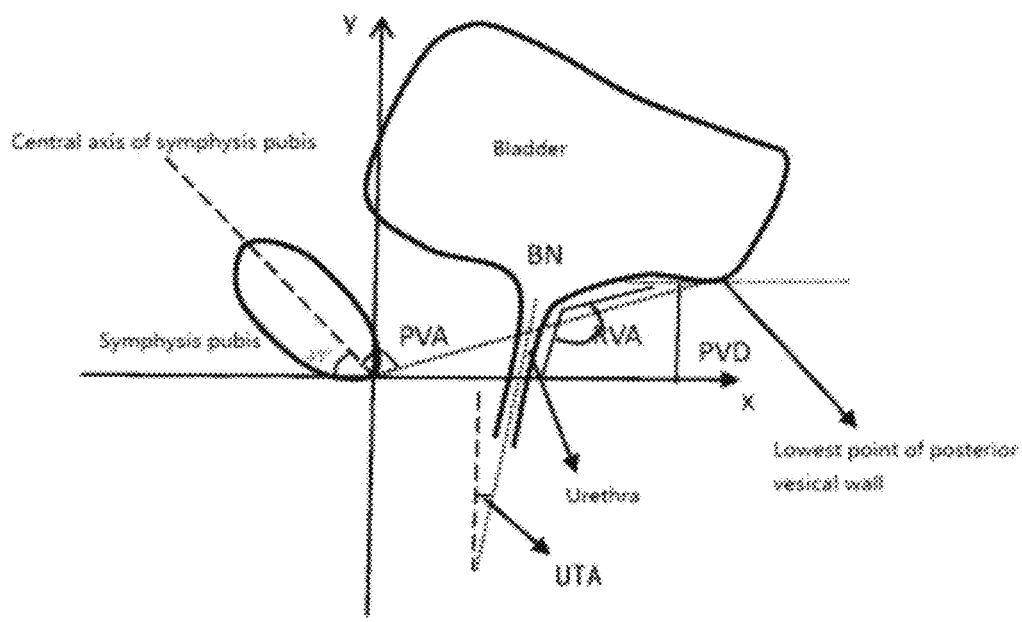

The anatomical structures of the above input items are schematically shown in FIG. 12 and FIG. 13. FIG. 12 schematically shows the parameter items of the pelvic floor, including the pubourethral angle PUA, the posterior urethrovesical angle RVA, the urethral tilt angle UTA, and the distance BSD from the symphysis pubis to the x axis.

Figure 14:
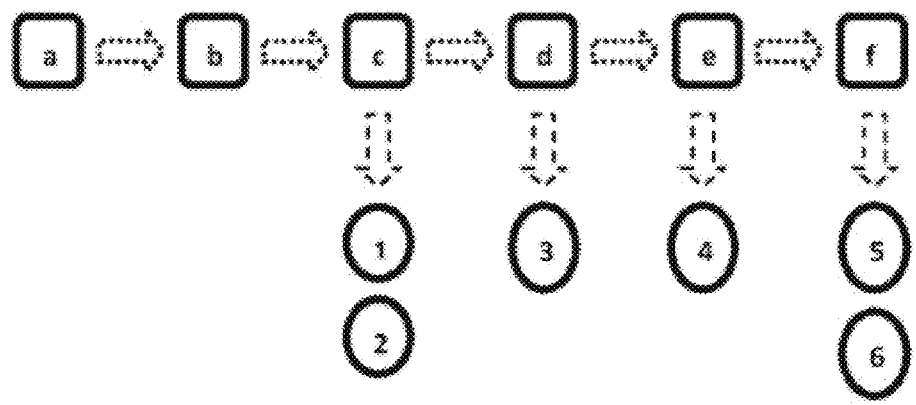
FIGS. 14 and 15 are schematic flowcharts of two embodiments, respectively.

FIG. 13 schematically shows the parameter items of the pelvic floor, including the pubovesical angle PVA, the posterior urethrovesical angle RVA, the urethral tilt angle UTA, and the distance PVD from the symphysis pubis to the xaxis. The items a) and b) may be used to determine the coordinate system. At this time, the user can sort these inputs according to personal habits, or choose not to change them. When a new qualified image is acquired, the user may input the above information through an input device in a pre-defined order (as shown in FIG. 14). As user input increases, the system will gradually update the measurement results until the measurement is completed.

As the inputted information increases, the measurement results will also be increased accordingly. The input order of the information items a to f may be preset, and may also be deleted as needed. The definitions of a to f and 1 to 6 are shown above. As shown in FIG. 14, after the position of (c) the urethrovesical junction is determined, the parameters (1) the angle PUA between the symphysis pubis and UVJ and (2) the distance BSD from UVJ to the X axis may be displayed; after the position of (d) the proximal end of the urethra is determined, the parameter (3) the urethral tilt angle UTA may be displayed; after the position of (e) the proximal end of posterior vesical wall is determined, the parameter (4) the retrovesical angle RVA may be displayed; and after the position of (f) the lowest point of posterior vesical wall is determined, the parameters (5) the pubovesical angle PVA and (6) the distance PVD from the lowest point of the posterior wall of the bladder to the X axis may be displayed.

Based on the above embodiment, the user may choose not to measure the angle PVA and the distance PVD. In this case, the measurement requirements will be simplified as follows:

(1) the angle PUA between the symphysis pubis and UVJ,
(2) the distance BSD from UVJ to X axis,
(3) the urethral tilt angle UTA, and
(4) the retrovesical angle RVA.

In this case, the information of the pelvic floor anatomical features that needs to be inputted in the feature set will also be changed, and a default measurement sequence may be generated, as follows. See FIG. 15.

(a) the lower boarder of SP,
(b) the central axis of SP,
(c) the urethrovesical junction (UVJ),
(d) the proximal end of urethra, and
(e) the proximal end of posterior vesical wall.

Figure 15:
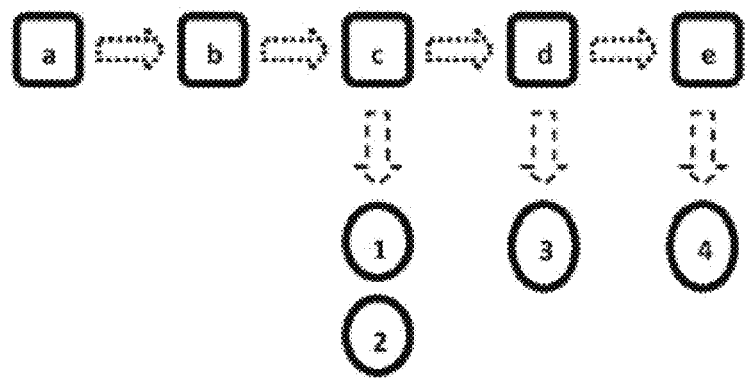

The entire simplified measurement process is shown in FIG. 15. After the position of (c) the urethrovesical junction is determined, the parameters (1) the angle PUA between the symphysis pubis and UVJ and (2) the distance BSD from UVJ to the X axis may be displayed; after the position of (d) the proximal end of the urethra is determined, the parameter (3) the urethral tilt angle UTA may be displayed; and after the position of (e) the proximal end of posterior vesical wall is determined, the parameter (4) the retrovesical angle RVA may be displayed.

In order to further simplify the operation process of the manual measurement or reduce the calculation of the automatic measurement, in one embodiment, the feature set may include at least the inferoposterior margin of the symphysis pubis and the central axis of the symphysis pubis. Furthermore, the first two anatomical features in the measurement sequence may be the inferoposterior margin of the symphysis pubis and the central axis of the symphysis pubis, so that the process of obtaining the reference coordinate system may be added to the measurement operation flow, thereby simplifying the flow operation. When the system performs the automatic identification and calculation based on the feature set and/or the measurement sequence, the system may first determine the relevant position of the reference coordinate system according to the feature set and/or measurement sequence, and then perform the calculation of specific parameters. Specifically, in one embodiment, the process of calculating the parameters related to the target tissue according to the measurement instruction to obtain the calculation result may include the following steps.

First, the image processing unit may determine the reference coordinate system based on the positions of the first two anatomical structures in the measurement sequence. The first two anatomical structures may be inferoposterior margin of the symphysis pubis and the central axis of the symphysis pubis.

Thereafter, according to the positions of the remaining anatomical features in the measurement sequence, and based on the determined reference coordinate system, the parameter to be measured may be calculated to obtain the corresponding calculation result.

The image processing unit may use one of the following two methods to determine the reference coordinate system according to the positions of the first two anatomical features in the measurement sequence.

In the first method, the inferoposterior margin of the symphysis pubis and the central axis of the symphysis pubis inputted by the user on the ultrasound image may be received, and a first Cartesian coordinate system, a second Cartesian coordinate system or a third coordinate system may be established according to the user input.

In the second method, the inferoposterior margin of the symphysis pubis and the central axis of the symphysis pubis may be automatically detected in the ultrasound image based on pattern recognition, and a first Cartesian coordinate system, a second Cartesian coordinate system or a third coordinate system may be established thereby. Regarding the specific identification methods, reference may be made to the related description above, which will not be described in detail here again.

Based on the reference coordinate system, according to the corresponding relationship between the parameter items in FIG. 12 and FIG. 13, the calculation results corresponding to the parameter items may be obtained by calculation.

The measurement sequence automatically generated by the system shown in FIG. 9 may be edited, so as to update the parameter items or measurement results. For example, in one embodiment, generating the measurement sequence according to the feature set and the determination order may include the following steps.

First, the image processing unit may automatically generate a preset measurement sequence based on the feature set and determination order. The preset measurement sequence may be automatically generated based on the parameter items inputted by the user in step 12 in FIG. 9.

Thereafter, the preset measurement sequence may be displayed on the display. It may be displayed in a text list or a prompt box.

Then, an editing instruction inputted by the user may be received through the input/output device. The editing instruction may represent an adjustment to the parameter items, or an adjustment to the anatomical features or determination order.

Thereafter, the preset measurement sequence may be updated according to the editing instruction to obtain the measurement sequence, which may be used to sequentially determine the position of each anatomical feature in the feature set to obtain the measurement instruction.

In the editing mode provided in the embodiment above, after the input is completed, the user can enter the editing mode. When the user edits these inputs, the measurement results may be updated in real time. When the user performs input or editing for the second frame, the system may not only display in real time the measurement results of the second frame, but also calculate in real time the changes of certain measurement values relative to the first frame, such as the relative change BND of BSD, the relative change URA of UTA, etc. The editing instruction in the embodiment above may include at least one of the operations: 1. adding or deleting the anatomical features in the feature set of the preset measurement sequence; 2. adjusting the determination order in the preset measurement sequence; and 3. editing or deleting the parameter items.

The embodiments shown in FIG. 8 and FIG. 9 and other various embodiments have mentioned the user's input of the parameter items. The "receiving at least one parameter item inputted by the user input" herein will not be limited to the user inputting the parameter item one by one, but may also include an input method of obtaining one or more parameter items by selecting a measurement mode or a measurement process preset by the system.

According to the various embodiments above, a fully automatic measurement may be achieved based on the feature set and/or the measurement sequence. Therefore, in one embodiment, a fully automatic measurement method is proposed, which can automatically determine the anatomical features such as the urethrovesical junction (UVJ), the proximal end of urethra, the proximal end of posterior vesical wall and the lowest point of posterior vesical wall, etc. The detection of these anatomical features may be performed on the basis of bladder segmentation tracking. The following uses several special anatomical feature detections as examples for illustration.

1. Bladder Segmentation Tracking

Figure 17:
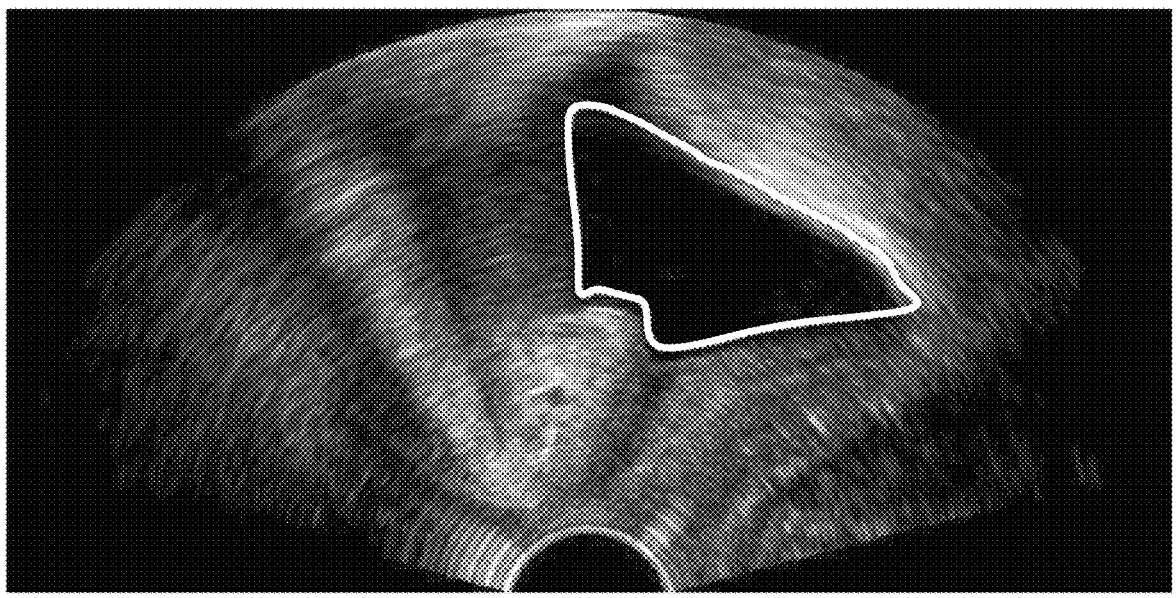
FIG. 17 shows an example of bladder contour segmentation.

The bladder may be segmented to detect other anatomical features using the contour of the bladder. FIG. 17 shows an example of bladder contour segmentation. In FIG. 17, the closed curve indicates the segmented bladder region. Common segmentation methods may include level set method, active contour model method, graph cut method, etc. For dynamic continuous image sequences, tracking methods may be used to improve accuracy and reduce the complexity of frame-by-frame calculations.

2. Urethrovesical Junction

Figure 20:
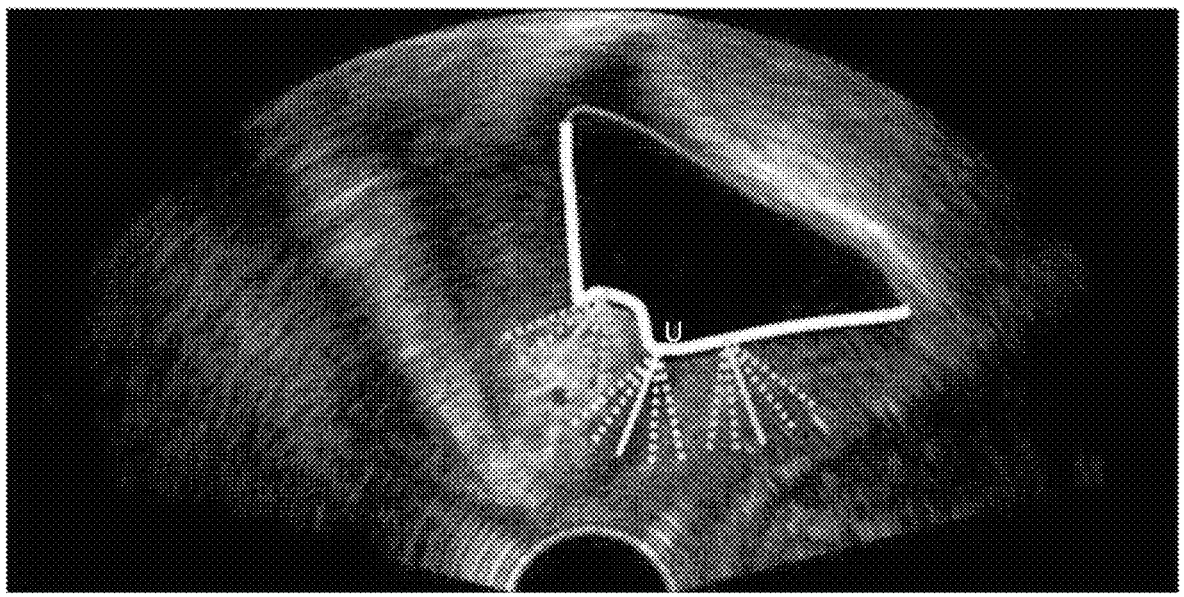
FIGS. 20 and 21 show the examples of Pubo Vesical Angle (PVA) and Pubo Vesical Distance (PVD) measurements.

FIG. 20 shows a schematic diagram of the urethrovesical junction (bladder neck) detection. As shown in FIG. 20, the part of the contour of the bladder close to the probe (as shown by the thick yellow part (the thick line frame) in the figure) may be sampled and searched at a certain interval. For each sampled position, the possibility of urethra in different directions within a certain range may be calculated, and the best position may be determined as the position of the urethra. The positions of the urethra and the bladder contour may be returned as the position value of the bladder neck. The detection method in this embodiment may be as follows: sampling the part of the contour of the bladder contour (as shown by the thick yellow part (the thick line frame) in the figure) close to the probe at a certain interval, for each sampled position, calculating the possibility of urethra in different directions within a certain range, determining the best position as the position of the urethra, and using the position of the urethra and the contour of the bladder as the position value of the bladder neck. For each candidate urethral position, the method for determining the best candidate position may be similar to the method for determination of the central axis of the symphysis pubis, as described below.

For each candidate urethral position, characteristics related to the structure of the urethra may be extracted. For example, the pixel values on the normal lines at both sides of the urethra at an interval along the urethral may be selected as the characteristics. The extracted characteristics may be inputted to a pre-trained detector and scored to obtain a group of scores. The candidate position with the highest score may be selected as the best urethral position.

3. The Lowest Point of Posterior Vesical Wall

Figure 22:
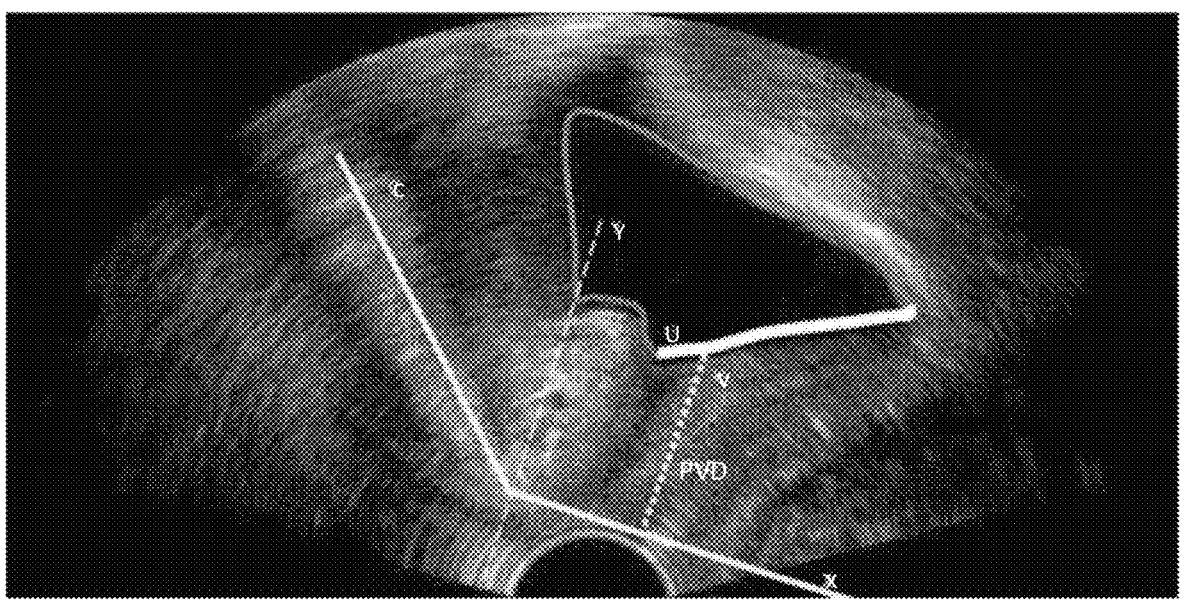
FIG. 22 schematically shows the detection of the lowest point of posterior vesical wall and the calculation of PVD.

The posterior vesical wall may refer to the point closest to the X axis (or the origin of the coordinate system, depending on the calculation method of PVD) on the right bladder contour at the urethrovesical junction. Since the bladder contour has been located, the rest is to search for the point closest to the X axis in a specific region on the bladder contour, as shown in FIG. 22. FIG. 22 schematically shows the detection of the lowest point of posterior vesical wall and the calculation of PVD. The positions of the X-axis and the Y-axis may be determined by the detected point S and the direction SC (the figure shows the situation where the first Cartesian coordinate system A is used). The position V of the point closest to the X axis of the posterior vesical wall (i.e., the thick yellow part in the figure) may be obtained according to the tracking result of the bladder contour and the detection result of the bladder neck. In this case, the Y coordinate of the point V may be the value of PVD.

4. Proximal End of Urethra

When the urethrovesical junction (UVJ) is obtained, the proximal end of the urethra may also be detected, i.e., a section of the urethra (for example, 2 cm) closer to the UVJ may be intercepted.

5. Proximal End of Posterior Vesical Wall

The proximal end of posterior vesical wall may be obtained according to the positions of the bladder contour and the urethrovesical junction, i.e., a point on the bladder contour close to the urethrovesical junction (for example, within 2 cm) may be selected as the proximal end of posterior vesical wall.

Calculation of the Parameters

After the main anatomical features are automatically detected, the calculation of the parameters may be simple.

Figure 18:
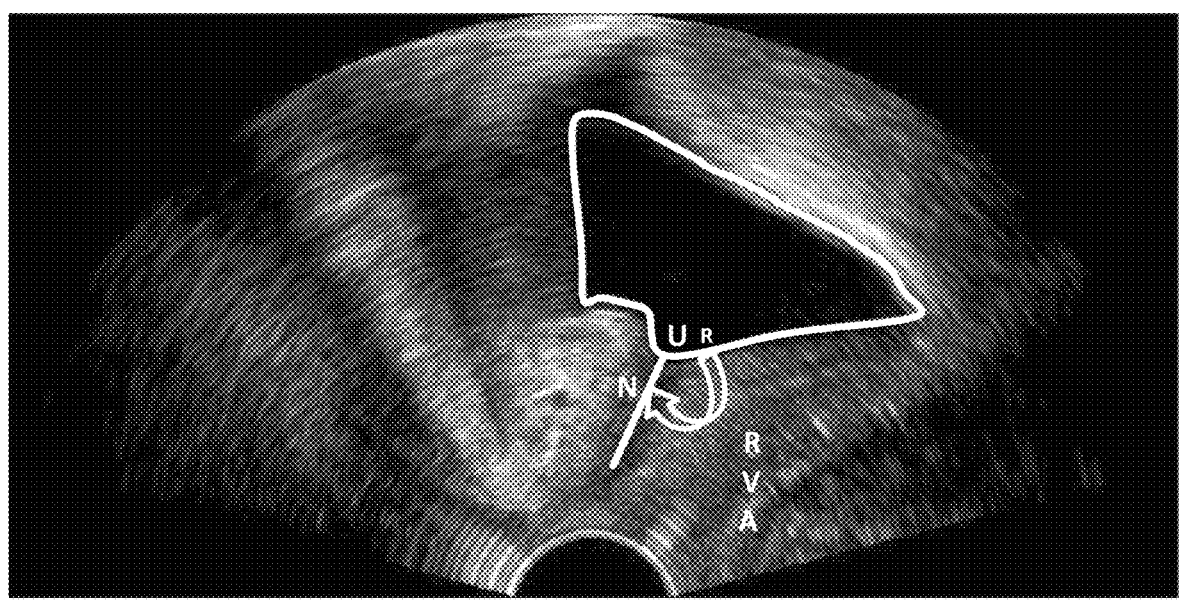
FIG. 18 shows an example of RVA measurement.

The RVA measurement is shown in FIG. 18. The system may use a level set method or similar method to automatically detect the contour of the bladder (or only detect the lower half of the contour of the bladder). Furthermore, the system may use a machine learning algorithm to automatically detect the position of the urethra (the yellow line in the figure). Based on the contours of the urethra and bladder, the system may automatically calculate the RVA from three points N, U and R.

Figure 19:
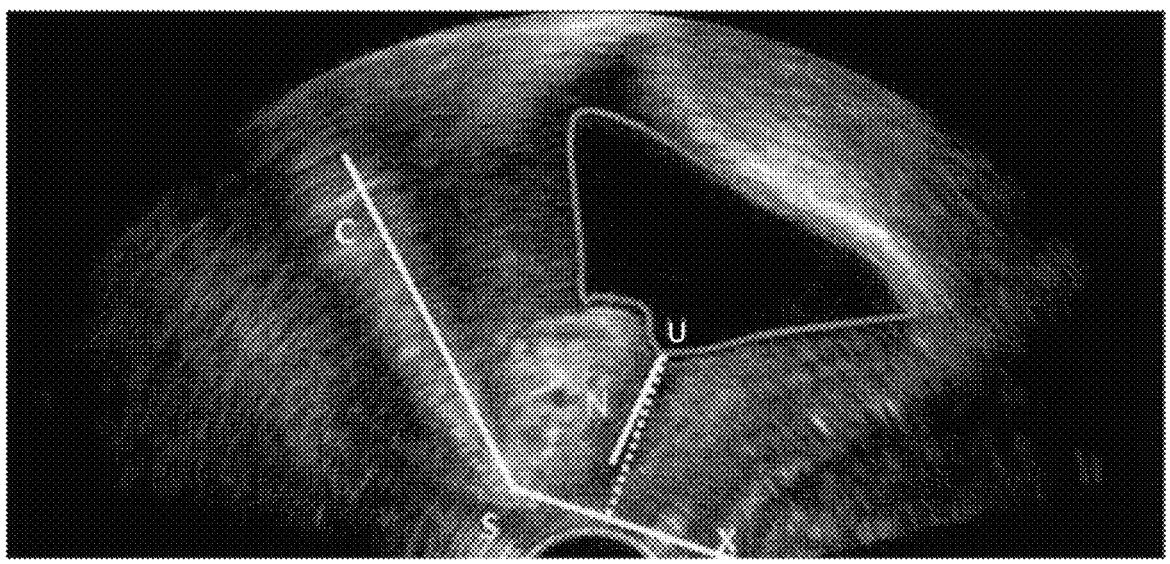
FIG. 19 shows an example of Urethral Tilt Angle (UTA) measurement.

The calculation of UTA is shown in FIG. 19, which schematically shows a schematic diagram of the automatic measurement of the UTA angle. The position of the X axis may be determined by the detected two points C and S, thereby obtaining the direction of the straight line I perpendicular thereto. The UTA angle is the angle between the urethra represented by the ray UN and the straight line I.

Figure 21:
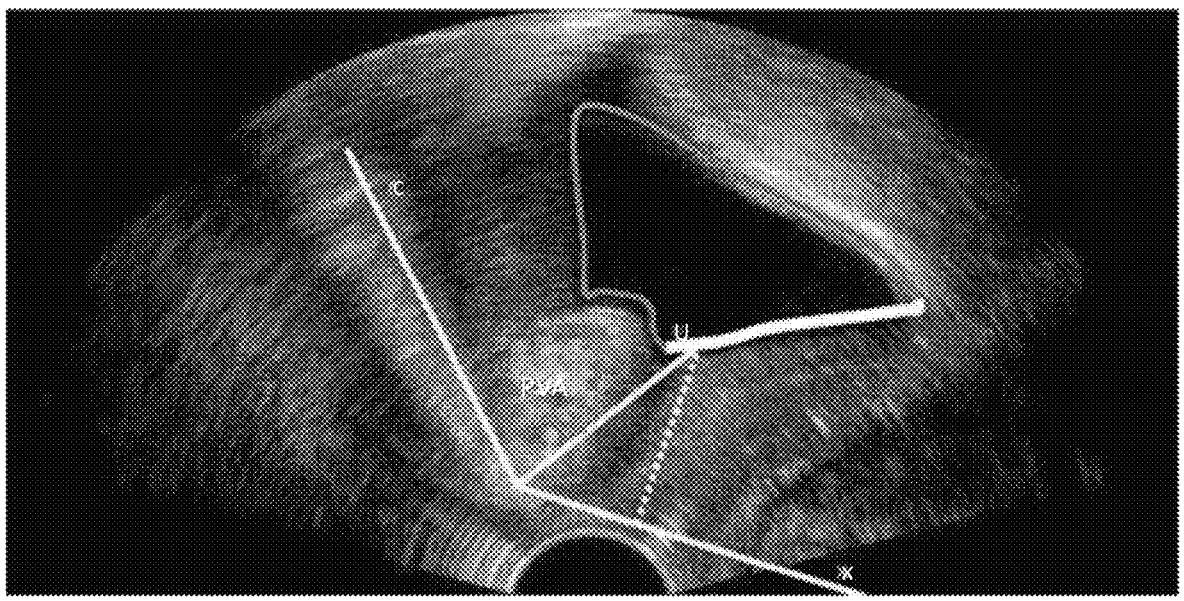

The calculation of PVA and PVD is shown in FIG. 20 and FIG. 21. FIG. 21 schematically shows the measurement of PVA. The value of PVA (as shown by the red arrow in the figure) may be determined according to the detected point S, the direction SC and the point V. The size of the PVA is independent of the coordinate system (that is, it is suitable for the first and second Cartesian coordinate systems above).

Figure 23:
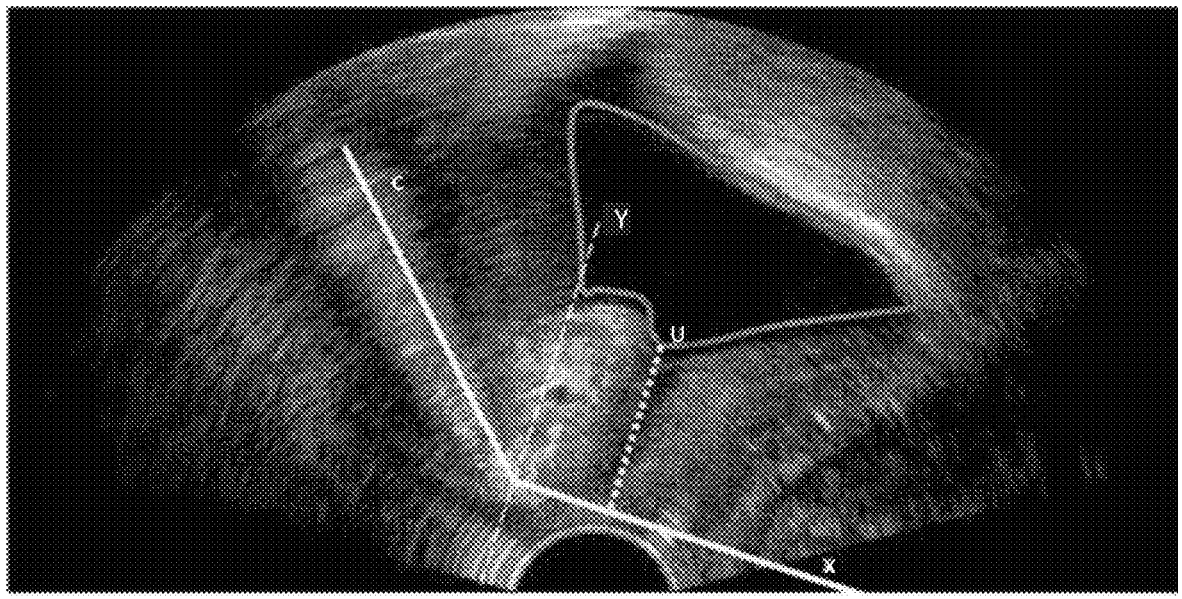
FIGS. 23 and 24 show the examples of Pubo Urethral Angle (PUA) and Bladder Neck-Symphyseal Distance (BSD) measurements.
Figure 24:
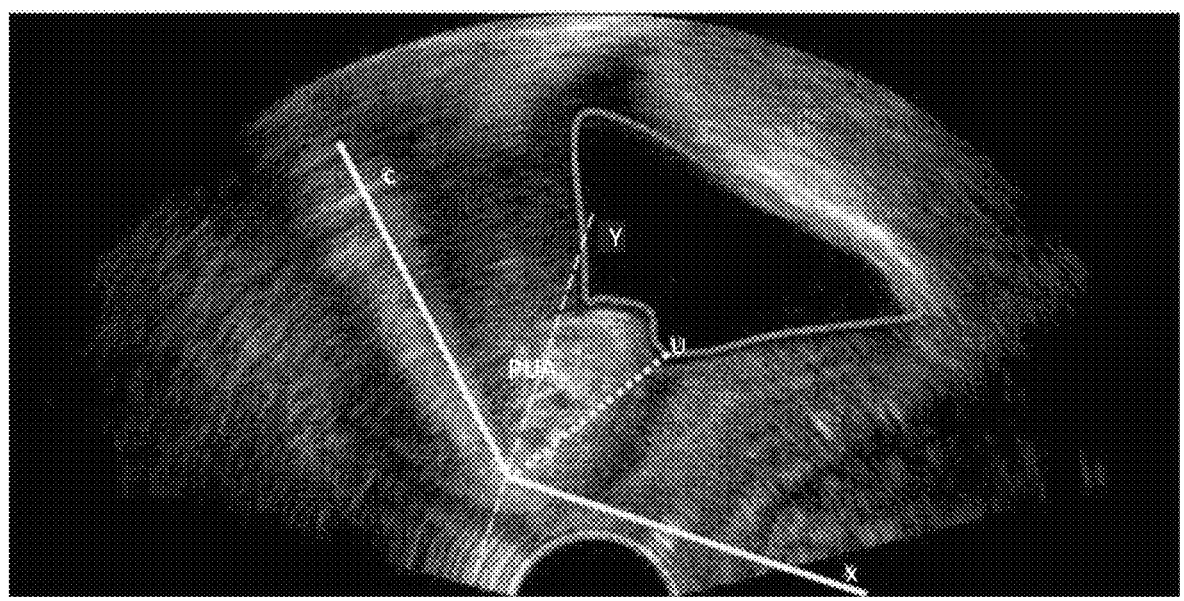

The measurements of PUA and BSD are shown in FIG. 23 and FIG. 24. FIG. 23 schematically shows the automatic measurement of BSD. The point U in the figure is the bladder neck that is automatically detected. The positions of the X axis and Y axis may be determined by the detected point S and the direction SC (the figure shows the situation where the first Cartesian coordinate system is used). In this case, the Y coordinate of the point U is the value of BSD. FIG. 24 schematically shows the measurement of PUA angle. The value of PUA (as shown by the red arrow in the figure) may be determined according to the detected point S, direction SC and point U. The size of the PUA is independent of the coordinate system (that is, it is suitable for the first and second Cartesian coordinate systems above).

In one embodiment, it may also be suitable for the comparative measurement of two frames of image for obtaining a dynamically changing measurement result. The specific scheme is as follows.

The displayed ultrasound image may include a first frame of image and a second frame of image. Therefore, the image processing unit may use the following method to obtain the measurement instruction based on the ultrasound image and calculate the parameter related to the target tissue according to the measurement instruction to obtain the calculation result:

the image processing unit may obtain a measurement instruction based on the first frame of image and calculate the parameter related to the target tissue according to the measurement instruction to obtain a first calculation result;

the image processing unit may obtain a measurement instruction based on the second frame of image and calculate the parameter related to the target tissue according to the measurement instruction to obtain a second calculation result;

the image processing unit may calculate a change of the second calculation result relative to the first calculation result; and the image processing unit may output the calculation results and the change.

These two frames of image may be obtained in the following way:

when multiple frames of ultrasound image are displayed on the display, a user's selection instruction may be received, and the ultrasound images may be obtained according to the selection instruction, where the ultrasound images include the first frame of image and the second frame of image, and in one embodiment, the two frames of image may be a rest frame image and a valsalva frame image.

Regarding the process of obtaining the first calculation result according to the first frame of image and the process of obtaining the second calculation result according to the second frame of image, reference may be made to the proves of obtaining the calculation result based on the ultrasound image above. The methods and steps may be partly or fully the same or similar. For example, by replacing the "ultrasonic image" in the above steps S230 and S240 with "first frame of image" and "second frame of image", the process of obtaining the first calculation result according to the first frame of image and the process of obtaining the second calculation result according to the second frame of image may be obtained.

In addition, after the input is completed, the user may enter the edit mode. When the user edits these inputs, the measurement results may be updated in real time. When the user inputs or edits on the second frame of image, the system may not only display the measurement results of the second frame of image in real time, but also calculate the change of certain measurement value relative to the first frame of image in real time, such as the relative change of BSD (i.e., the bladder neck descend BND), the relative change of UTA (i.e., the urethral rotation angle URA), and the relative change of PVD (i.e., the bladder wall descend BWD), etc. When the measurement of the second frame of image is completed, if the user edits the input of the first frame, the dynamic change as shown above will also be updated and displayed in real time.

In the embodiments above, in addition to intelligently assisting manual measurement, the ultrasound imaging system may also support fully automatic measurement, i.e., all anatomical features may be automatically detected by algorithms and the values of all parameter may be automatically obtained according to the positions of the anatomical features. In the case that the parameter on a single frame of ultrasound image is obtained by a fully automatic method, the dynamic change of the parameters may also be automatically obtained accordingly.

In addition, in one embodiment, based on the calculation result of the pelvic floor tissue obtained above, the pelvic floor function may be evaluated to obtain an evaluation level. The International Urinary Control Association (ICS) has released a quantitative rating system for pelvic floor prolapse procedures, which is referred to as the POP-Q system. The POP-Q system grades the pelvic floor prolapse into five levels from 0 degree to IV degree through surgical examination. In the present embodiment, a quantitative analysis may be performed on the prolapse of the pelvic floor organs using ultrasound examination. After the measurement is completed, the system may obtain a score based on a formula and the measurement results to present the degree or grade of the pelvic floor dysfunction. This score may be converted into the equivalent ICS POP-Q score.

Regarding the evaluation of the pelvic floor function, in the present embodiment, the following methods may be used.

In the first method, the system may provide default evaluation rules, which may be mapped by maximizing the value of PVD under Valsalva, i.e., when PVD=1 cm, the equivalent POP-Q is level 1;

when $-2$ cm<PVD <1 cm, the equivalent POP-Q is level 2; and when PVD <$-2$ cm, the equivalent POP-Q is 3 or more.

For example, in one embodiment, the evaluation level may be obtained based on the default evaluation rules according to the calculation result of the parameters. The default evaluation rules here may be mapped by maximizing the calculation results of specific parameters calculated on a specific frame. The specific frame may include a Valsalva frame, and the specific parameter may include the PVD.

In the second method, the user may customize the evaluation rules and formulas with reference to the default rating method. For example, it may be possible to comprehensively consider the results of both BSD and PVD or change the evaluation threshold. For example, in one embodiment, the evaluation level may be obtained based on the values of BSD and PVD in the calculation results, and may be outputted. In addition, in one embodiment, the image processing unit may receive the adjustment of the user to the evaluation rules which are used for determining the evaluation level. Based on the adjusted evaluation rules, the evaluation level may be determined according to the calculation results obtained by the methods above, and be outputted.

In the third method, the system may provide a method based on machine learning to automatically achieve the comprehensive grading of prolapse, which is described below.

(a) Two-dimensional images, the measurement results of the two-dimensional images and the scores to the two-dimensional images manually given by the doctor may be collected offline or online;

(b) The system may automatically perform a mathematical correlation analysis on the scores given by the doctor, the measurement results and the images to establish a correlation relationship. There may be many analysis methods, such as linear regression method, Kalman filtering method, Gaussian process regression method, support vector regression method and other regression analysis methods. Alternatively, the deep neural network method or the like may also be used.

(c) After establishing the correlation relationship, the system may obtain a rating score comprehensively based on the measurement results. In the case that the user objects to the score, the user can modify the score manually. The system may further refine the correlation relationship after receiving the feedback so as to obtain a score that better meets the user's expectations. Anyway, when the ultrasound imaging system performs the method based on machine learning above, it may input multiple image samples, the calculation results of the parameters calculated on the image samples and the corresponding evaluation levels into the detector where the mathematical correlation analysis may be performed thereon to obtain a machine model, and automatically obtain the evaluation level according to the calculation results actually obtained on the ultrasound image using the machine model. The evaluation levels herein may be presented by number such as 0-100, percentage, or quantified staged indexes (such as 1, 2, 3, etc.), etc.

In step S250, the image processing unit may output the calculation results corresponding to the parameters. The calculation results may be outputted by print or display.

In one embodiment, when a parameter is calculated, the calculation result may be displayed immediately. The calculation and result display of the parameters may increase with the increase of the user input. The system may calculate the parameters one by one and display them in real time. When the user perform the measurement on the second frame of image, the system may additionally calculate the change of the parameter of the second frame relative to the first frame of image in the same coordinate system, and displays it in real time.

The embodiments above propose convenient and fast parameter measurement methods based on two-dimensional or three-dimensional ultrasound images, which may be applied to the measurement of pelvic floor parameters. The methods may automatically establish the measurement coordinate system and make use of the correlation relationship between the parameters of the pelvic floor to minimize the input during the measurement, thereby improving the measurement efficiency and reducing the measurement errors. The methods may also calculate the relative change of the parameter between two frames of images according to user needs, and automatically obtain the dysfunction score or grade of the object being examined comprehensively based on these parameters and their relative changes. The methods may also support online or offline learning the scoring manner of the user so as to achieve automatic scoring.

Through the description of the above embodiments, those skilled in the art will clearly understand that the methods in the embodiments above may be implemented by software and a universal hardware platform, or implemented by hardware. Based on this understanding, the essential part or the part contributing to the existing technology of the technical solutions of the present disclosure may be embodied in the form of a software product, which may be carried on a non-volatile computer-readable storage media (such as ROM, magnetic disk, optical disk, hard disk, server cloud space) and include multiple instruction which may enable a terminal device (which may be a mobile phone, a computer, a server, or a network device, etc.) to implement the system structures and methods of the embodiments of the present disclosure.

Only several implementations have been described in the embodiments above, and the description thereof is relative specific and detailed. However, it cannot be understood as a limitation to the scope of the present disclosure. It should be noted that, for those of ordinary skill in the art, several modifications and improvements may be made without departing from the concept of the present disclosure, which all belong to the protection scope of the present disclosure. Therefore, the protection scope of the present disclosure shall be determined by to the appended claims.

The invention claimed is:

1. A method for measuring a parameter in an ultrasound image, comprising:
    obtaining, by an image processor, an ultrasound image by detecting ultrasound signals from a target tissue with an ultrasound probe, wherein the ultrasound image contains an area representing the target tissue;
    displaying, by the image processor, the ultrasound image on a display;
    obtaining, by the image processor, a measurement instruction based on the ultrasound image and according to a user input, by:
        receiving a parameter item from the user input, wherein the parameter item corresponds to a parameter of the target tissue, wherein the parameter is calculated based on at least two anatomical features;
        obtaining a feature set including a plurality of anatomical features associated with the parameter item, wherein the plurality of anatomical features comprise one or more anatomical features existing in the target tissue and/or one or more of an anatomical reference line or anatomical reference position that is artificially defined for measurement of the target tissue; and
        determining a position in the ultrasound image of each of the anatomical features in the feature set to obtain the measurement instruction, wherein the measurement instruction comprises a measurement sequence of the anatomical features;
    automatically detecting, by the image processor, an inferoposterior margin of symphysis pubis and a central axis of symphysis pubis in the ultrasound image based on pattern recognition, wherein the automatically detecting comprises:
        determining a starting point of the central axis of symphysis pubis according to the inferoposterior margin of symphysis pubis;
        determining a candidate ray representing the central axis of symphysis pubis starting from the starting point, wherein the candidate ray has an initial deflection angle;
        obtaining multiple candidate rays starting from the starting point in a predetermined range centered on the initial deflection angle in a predetermined angle interval;
        extracting pixel characteristics of the multiple candidate rays; and
        determining the central axis of symphysis pubis from the multiple candidate rays according to the pixel characteristics;
    determining, by the image processor, a reference coordinate system based on the inferoposterior margin of symphysis pubis and the central axis of symphysis pubis, for performing the measurement instruction;
    calculating, by the image processor, a parameter related to the target tissue according to the measurement instruction and based on the determined reference coordinate system to obtain a calculation result; and
    outputting, by the image processor, the calculation result.

2. The method of claim 1, wherein the target tissue comprises a pelvic floor tissue.

3. The method of claim 1, wherein the ultrasound image comprises an anterior pelvic ultrasound image, a middle pelvic ultrasound image, or a posterior pelvic ultrasound image.

4. The method of claim 1, wherein determining the position in the ultrasound image of each of the anatomical features in the feature set to obtain the measurement instruction comprises:
determining a determination order of the anatomical features in the feature set;
generating the measurement sequence based on the feature set and the determination order; and
sequentially determining the position of each of the anatomical features in the feature set according to the measurement sequence to obtain the measurement instruction.

5. The method of claim 1, wherein determining the position in the ultrasound image of each of the anatomical features in the feature set to obtain the measurement instruction comprises:
receiving sequential determination operations of the user to the anatomical features in the feature set on the ultrasound image; and
obtaining the measurement instruction according to the determination operations inputted sequentially by the user, wherein the determination operations are orderly operations performed according to the measurement sequence.

6. The method of claim 4, further comprising: prompting the feature set or the measurement sequence for displaying.

7. The method of claim 6, wherein prompting the feature set or the measurement sequence comprises:
generating an anatomical schematic diagram of the target tissue based on knowledge of tissue anatomy, displaying the anatomical schematic diagram, and marking the anatomical features in the feature set or the measurement sequence on the anatomical schematic diagram.

8. The method of claim 1, wherein outputting, by the image processor, the calculation result comprises:
displaying the calculation result after the calculation result of the parameter is obtained.

9. The method of claim 1, wherein determining, by the image processor, the reference coordinate system comprises,
determining a first Cartesian coordinate system, by: determining that a 45-degree angle line of a second quadrant of the first Cartesian coordinate system is the central axis of symphysis pubis, and determining that the X axis of the first Cartesian coordinate system is at 45-degree angle from the central axis of symphysis pubis, and
determining a second Cartesian coordinate system, by: determining that the X axis of the second Cartesian coordinate system is the central axis of symphysis pubis.

10. The method of claim 1, wherein, the feature set comprises at least an inferoposterior margin of symphysis pubis and a central axis of symphysis pubis.

11. The method of claim 4, wherein generating the measurement sequence based on the feature set and the determination order comprises:
automatically generating a preset measurement sequence based on the feature set and the determination order;
displaying the preset measurement sequence;
receiving an editing instruction inputted by a user; and
updating the preset measurement sequence according to the editing instruction to obtain the measurement sequence.

12. The method of claim 9, wherein determining the reference coordinate system further comprises:
receiving an inferoposterior margin of symphysis pubis and a central axis of symphysis pubis inputted by a user on the ultrasound image, and establishing the first Cartesian coordinate system or the second Cartesian coordinate system according to the input of the user.

13. The method of claim 12, wherein automatically detecting the inferoposterior margin of symphysis pubis and the central axis of symphysis pubis in the ultrasound image based on the pattern recognition comprises:
inputting positive image samples containing inferoposterior margins of symphysis pubis and negative image samples not containing inferoposterior margins of symphysis pubis into a detector to perform a training;
obtaining a recognition model based on the training; and
automatically detecting the inferoposterior margin of symphysis pubis in the ultrasound image using the recognition model.

14. The method of claim 12, wherein receiving the inferoposterior margin of symphysis pubis and the central axis of symphysis pubis inputted by the user on the ultrasound image comprises:
receiving a click input to determine the inferoposterior margin of symphysis pubis;
determining a starting point of a candidate center axis when a trackball or a mouse or a touch contact with a display screen starts moving; and
when the trackball, the mouse, or the touch contact with the display screen stops moving, determining an ending point of the candidate center axis as the central axis of symphysis pubis.

15. The method of claim 1, wherein the ultrasound image comprises at least one of a rest frame image or a valsalva frame image.

16. The method of claim 1, wherein,
the ultrasound image comprises a first frame of image and a second frame of image,
obtaining, by the image processor, the measurement instruction based on the ultrasound image comprises:
obtaining a first measurement instruction based on the first frame of image; and
obtaining a second measurement instruction based on the second frame of image;
calculating, by the image processor, a parameter related to the target tissue according to the measurement instruction and based on the determined reference coordinate system to obtain a calculation result comprises:
calculating the parameter according to the first measurement instruction to obtain a first calculation result;
calculating the parameter according to the second measurement instruction to obtain a second calculation result;
calculating a change of the second calculation result relative to the first calculation result; and
outputting the change.

17. The method of claim 1, further comprising:
obtaining an evaluation level according to the calculation result; and
outputting the evaluation level, wherein the evaluation level comprises a number, a percentage, or an index.

18. The method of claim 17, wherein obtaining the evaluation level according to the calculation result comprises at least one of:
- receiving an adjustment from a user to an evaluation rule used for determining the evaluation level, adjusting the evaluation rule, and determining the evaluation level based on the calculation result according to the adjusted evaluation rule;
- obtaining the evaluation level based on the calculation result according to a default evaluation rule, wherein the default evaluation rule is obtained by maximizing the calculation result of a specific parameter calculated on a specific frame; or
- inputting multiple image samples, the calculation results of the parameters calculated on the image samples, and corresponding evaluation levels into a detector to perform a mathematical correlation analysis to obtain a machine model, and automatically obtaining the evaluation level according to the calculation result using the machine model.

19. An ultrasound imaging system, comprising:
- a probe;
- a transmitting circuit which excites the probe to transmit an ultrasonic beam to a target tissue through the probe;
- a receiving circuit which receives ultrasonic echoes of the ultrasonic beam through the probe to obtain ultrasonic echo signals;
- a processor which obtains an ultrasound image based on the ultrasound echo signals; and
- a display which displays the ultrasound image; wherein the processor further
    - obtains a measurement instruction based on the ultrasound image and according to a user input, by:
        - receiving a parameter item from the user input, wherein the parameter item corresponds to a parameter of the target tissue, wherein the parameter is calculated based on at least two anatomical features;
        - obtaining a feature set including a plurality of anatomical features associated with the parameter item, wherein the plurality of anatomical features comprise one or more anatomical features existing in the target tissue and/or one or more of an anatomical reference line or anatomical reference position that is artificially defined for measurement of the target tissue; and
        - determining a position in the ultrasound image of each of the anatomical features in the feature set to obtain the measurement instruction, wherein the measurement instruction comprises a measurement sequence of the anatomical features;
    - automatically detects an inferoposterior margin of symphysis pubis and a central axis of symphysis pubis in the ultrasound image based on pattern recognition, wherein the automatically detecting comprises:
        - determining a starting point of the central axis of symphysis pubis according to the inferoposterior margin of symphysis pubis;
        - determining a candidate ray representing the central axis of symphysis pubis starting from the starting point, wherein the candidate ray has an initial deflection angle;
        - obtaining multiple candidate rays starting from the starting point in a predetermined range centered on the initial deflection angle in a predetermined angle interval;
        - extracting pixel characteristics of the multiple candidate rays; and
        - determining the central axis of symphysis pubis from the multiple candidate rays according to the pixel characteristics;
    - determines a reference coordinate system based on the inferoposterior margin of symphysis pubis and the central axis of symphysis pubis, for performing the measurement instruction;
    - calculates a parameter related to the target tissue according to the measurement instruction and based on the determined reference coordinate system to obtain a calculation result; and
    - outputs the calculation result.

* * * * *